(12) United States Patent
Serdarevic et al.

(10) Patent No.: US 11,982,815 B2
(45) Date of Patent: *May 14, 2024

(54) LIGHT CONTROL DEVICES AND METHODS FOR REGIONAL VARIATION OF VISUAL INFORMATION AND SAMPLING

(71) Applicant: Aperture in Motion, LLC, Phoenix, AZ (US)

(72) Inventors: Olivia Serdarevic, Goshen, NY (US); Edward Yavitz, Loves Park, IL (US)

(73) Assignee: Aperture in Motion, LLC, Phoenix, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/080,313

(22) Filed: Dec. 13, 2022

(65) Prior Publication Data

US 2023/0152589 A1 May 18, 2023

Related U.S. Application Data

(63) Continuation of application No. 17/948,846, filed on Sep. 20, 2022, now Pat. No. 11,536,978, which is a (Continued)

(51) Int. Cl.
*A61B 3/10* (2006.01)
*A61B 3/00* (2006.01)
(Continued)

(52) U.S. Cl.
CPC ........ *G02B 27/0172* (2013.01); *A61B 3/0008* (2013.01); *A61B 3/10* (2013.01);
(Continued)

(58) Field of Classification Search
CPC ....... A61B 3/0008; A61B 3/024; A61B 3/028; A61B 3/10; A21F 2/14; A21F 2/1451;
(Continued)

(56) References Cited

U.S. PATENT DOCUMENTS 5,444,559 A 8/1995 Warnar et al.
5,662,706 A 9/1997 Legerton et al.
(Continued)

FOREIGN PATENT DOCUMENTS

JP 2007185324 A 7/2007
JP 4387194 B2 12/2009

OTHER PUBLICATIONS

International Search Report and Written Opinion in International Application No. PCT/US18/66007, dated Feb. 15, 2019.
(Continued)

*Primary Examiner* — Adam J Snyder
(74) *Attorney, Agent, or Firm* — Duane Morris LLP

(57) ABSTRACT

Exemplary light control devices and methods provide a regional variation of visual information and sampling ("V-VIS") of an ocular field of view that improves or stabilizes vision, ameliorates a visual symptom, reduces the rate of vision loss, or reduces the progression of an ophthalmic or neurologic condition, disease, injury or disorder. The V-VIS devices and methods generate a moving aperture effect anterior to a retina that samples and delivers to the retina environmental light from an ocular field of view at a sampling rate between 50 hertz and 50 kilohertz. Certain of these V-VIS devices and methods may be combined with augmented or virtual reality, vision measurement, vision monitoring, or other therapies including, but not limited to, pharmacological, gene, retinal replacement and stem cell therapies.

3 Claims, 17 Drawing Sheets

Related U.S. Application Data continuation of application No. 17/392,957, filed on Aug. 3, 2021, now Pat. No. 11,480,798, which is a continuation of application No. 16/933,376, filed on Jul. 20, 2020, now Pat. No. 11,106,043, which is a continuation of application No. 16/544,102, filed on Aug. 19, 2019, now Pat. No. 10,768,431, which is a continuation-in-part of application No. 16/418,444, filed on May 21, 2019, now Pat. No. 10,386,646, which is a continuation of application No. 16/222,476, filed on Dec. 17, 2018, now Pat. No. 10,330,939, which is a continuation of application No. 15/903,923, filed on Feb. 23, 2018, now Pat. No. 10,175,490.

(60) Provisional application No. 62/608,039, filed on Dec. 20, 2017.

(51) Int. Cl.

| | | |
|---|---|---|
| *A61F 2/14* | (2006.01) | |
| *A61F 2/16* | (2006.01) | |
| *A61F 11/04* | (2006.01) | |
| *A61N 1/30* | (2006.01) | |
| *G02B 27/01* | (2006.01) | |
| *G06T 19/00* | (2011.01) | |
| *A61B 3/024* | (2006.01) | |
| *A61B 3/028* | (2006.01) | |
| *A61F 9/00* | (2006.01) | |
| *A61H 5/00* | (2006.01) | |
| *A61N 5/06* | (2006.01) | |
| *G02B 26/08* | (2006.01) | |
| *G02C 7/04* | (2006.01) | |
| *G02C 7/16* | (2006.01) | |
| *G02C 11/00* | (2006.01) | |

(52) U.S. Cl.
CPC .......... *A61F 2/1451* (2015.04); *A61F 2/1613* (2013.01); *A61F 2/1624* (2013.01); *A61F 11/04* (2013.01); *A61N 1/30* (2013.01); *G06T 19/006* (2013.01); *A61B 3/024* (2013.01); *A61B 3/028* (2013.01); *A61F 2/14* (2013.01); *A61F 2/16* (2013.01); *A61F 2/1632* (2013.01); *A61F 2/1635* (2013.01); *A61F 2002/1696* (2015.04); *A61F 2002/1699* (2015.04); *A61F 9/00* (2013.01); *A61F 2250/0001* (2013.01); *A61H 5/00* (2013.01); *A61H 2205/024* (2013.01); *A61N 5/0622* (2013.01); *A61N 2005/0648* (2013.01); *G02B 26/08* (2013.01); *G02B 2027/012* (2013.01); *G02B 2027/0178* (2013.01); *G02C 7/04* (2013.01); *G02C 7/16* (2013.01); *G02C 11/10* (2013.01)

(58) Field of Classification Search
CPC ........ A21F 2/16; A21F 2/1613; A21F 2/1624; A21F 2/1632; A21F 2/1635; A61F 9/00; A61F 11/04; A61F 2002/1696; A61F 2002/1699; A61F 2250/0001; A61H 5/00; A61H 2205/024; A61N 1/30; A61N 5/0622; A61N 2005/0648; G02B 26/08; G02B 27/0172; G02B 2027/012; G92B 2027/0178; G02C 7/04; G02C 7/16; G02C 11/10; G06T 19/006
See application file for complete search history.

(56) References Cited

U.S. PATENT DOCUMENTS

| | | |
|---|---|---|
| 5,965,330 A | 10/1999 | Evans et al. |
| 6,160,527 A | 12/2000 | Morishima |
| 6,992,718 B1 | 1/2006 | Takahara |
| 7,360,896 B2 | 4/2008 | Liang et al. |
| D656,526 S | 3/2012 | Christie et al. |
| 8,376,548 B2 | 2/2013 | Schultz |
| 8,462,418 B1 | 6/2013 | Gat et al. |
| 8,548,290 B2 | 10/2013 | Travers et al. |
| 8,582,209 B1 | 11/2013 | Amirparviz |
| 8,649,099 B2 | 2/2014 | Schultz et al. |
| 9,400,395 B2 | 7/2016 | Travers et al. |
| 9,857,884 B2 | 1/2018 | Arai et al. |
| 10,146,054 B2 | 12/2018 | Martinez |
| 10,175,490 B1 * | 1/2019 | Serdarevic ............ A61F 2/1613 |
| 10,330,939 B1 * | 6/2019 | Serdarevic ........... A61B 1/0655 |
| 10,386,646 B1 * | 8/2019 | Serdarevic ............. A61B 3/005 |
| 10,768,431 B2 * | 9/2020 | Serdarevic ............. G02C 11/10 |
| 11,106,043 B2 * | 8/2021 | Serdarevic ............ G06T 19/006 |
| 11,480,798 B2 * | 10/2022 | Serdarevic ............... G02C 7/04 |
| 11,536,978 B1 * | 12/2022 | Serdarevic .............. A61F 11/04 |
| 2005/0068497 A1 | 3/2005 | Hanebuchi et al. |
| 2006/0033879 A1 | 2/2006 | Covannon et al. |
| 2009/0146583 A1 | 6/2009 | Bhadri et al. |
| 2010/0128221 A1 | 5/2010 | Muller et al. |
| 2010/0201897 A1 | 8/2010 | Saitoh |
| 2011/0074937 A1 | 3/2011 | Nakahata |
| 2011/0204209 A1 | 8/2011 | Barrows |
| 2011/0285967 A1 | 11/2011 | Gollier |
| 2012/0295202 A1 | 11/2012 | Sano |
| 2013/0222384 A1 | 8/2013 | Futterer |
| 2013/0229710 A1 | 9/2013 | Watanabe |
| 2014/0085439 A1 | 3/2014 | Niwano |
| 2014/0111558 A1 | 4/2014 | Ishitani |
| 2014/0160471 A1 | 6/2014 | Ueno et al. |
| 2014/0254007 A1 | 9/2014 | Ma |
| 2015/0029317 A1 | 1/2015 | Kim |
| 2015/0178939 A1 | 6/2015 | Bradski |
| 2015/0205126 A1 | 7/2015 | Schowengerdt |
| 2015/0235473 A1 | 8/2015 | Schowengerdt |
| 2015/0312560 A1 | 10/2015 | Deering |
| 2015/0363976 A1 | 12/2015 | Henson |
| 2016/0048016 A1 | 2/2016 | Crane et al. |
| 2016/0106588 A1 | 4/2016 | Srinivasan et al. |
| 2016/0116979 A1 | 4/2016 | Border |
| 2016/0131912 A1 | 5/2016 | Border |
| 2016/0140887 A1 | 5/2016 | Kim |
| 2016/0147067 A1 | 5/2016 | Hua et al. |
| 2016/0270656 A1 | 9/2016 | Samec |
| 2017/0075119 A1 | 3/2017 | Schultz |
| 2017/0108702 A1 | 4/2017 | Rabner |
| 2017/0189233 A1 | 7/2017 | Dewey et al. |
| 2017/0273551 A1 | 9/2017 | Chung |
| 2017/0336626 A1 | 11/2017 | Hayashi et al. |
| 2017/0371160 A1 | 12/2017 | Schultz |
| 2018/0003977 A1 | 1/2018 | Mir et al. |
| 2018/0101998 A1 | 4/2018 | Pierce et al. |
| 2018/0129072 A1 | 5/2018 | Aschwanden et al. |
| 2018/0182307 A1 | 6/2018 | Tseng et al. |
| 2018/0220888 A1 | 8/2018 | Tumlinson |
| 2022/0268893 A1 | 8/2022 | Pacala et al. |

OTHER PUBLICATIONS

A Supplementary European Search Report issued by the European Patent Office dated Nov. 22, 2021, in European Application No. 18893204 (2 pages).

* cited by examiner

LIGHT CONTROL DEVICES AND METHODS FOR REGIONAL VARIATION OF VISUAL INFORMATION AND SAMPLING

CROSS-REFERENCE TO RELATED APPLICATION

This application is a continuation of and claims the benefit of priority to U.S. application Ser. No. 17/948,846, filed Sep. 20, 2022, which is a continuation of and claims the benefit of priority to U.S. application Ser. No. 17/392,957, filed Aug. 3, 2021 (now U.S. Pat. No. 11,480,798), which is a continuation of and claims the benefit of priority to U.S. application Ser. No. 16/933,376, filed Jul. 20, 2020 (now U.S. Pat. No. 11,106,043), which is a continuation of and claims the benefit of priority to U.S. application Ser. No. 16/544,102, filed Aug. 19, 2019 (now U.S. Pat. No. 10,768,431), which is a continuation-in-part of and claims the benefit of priority to U.S. application Ser. No. 16/418,444, filed May 21, 2019 (now U.S. Pat. No. 10,386,646), which is a continuation of and claims the benefit of priority to U.S. application Ser. No. 16/222,476, filed Dec. 17, 2018 (now U.S. Pat. No. 10,330,939), which is a continuation of and claims the benefit of priority to U.S. application Ser. No. 15/903,923, filed Feb. 23, 2018 (now U.S. Pat. No. 10,175,490), which claims the benefit of priority to U.S. Provisional Application No. 62/608,039, filed Dec. 20, 2017. The disclosures of each of these applications are incorporated herein by reference in their entireties for all purposes

TECHNICAL FIELD

The disclosed embodiments relate to light control devices and methods for regional variation of visual information and sampling.

BACKGROUND

The retina is the part of the eye that responds to light from an ocular field of view and converts the light to signals to begin image processing. Visual processing continues in the brain where the retinal visual information is integrated spatially, temporally and with ocular movements to achieve visual perception of the ocular field of view. An optical axis is a straight line perpendicular to the front of the eye and extending through a center of the pupil, defined herein as coaxial.

SUMMARY

In some examples, a light control device is configured to move optically one or more apertures anterior to a retina of an eye between one or more positions anterior to the retina that are non-coaxial with a center of a pupil and a position anterior to the retina that is coaxial with the center of the pupil. The one or more apertures are moved at a rate between 50 hertz and 50 kilohertz, and the light control device produces a regional variation of visual information and sampling of an ocular field of view.

In additional examples, anterior to the retina can include one of extraocular, intracorneal or intraocular placement. Further, the light control device can move the one or more apertures electro-optically through one or more see-through displays placed anterior to the retina. The one or more see-through displays of the V-VIS device can be further configured to display at least one of an augmented reality image, a virtual reality image, or a combination of an augmented and virtual reality images.

The light device can also include one or more waveguides, and the light control device can move the one or more apertures using the one or more waveguides. In further examples, the one or more waveguides can be arranged in at least one of vertically stacked in layers, adjacent to one another in a single layer, or holographically multiplexed.

In some examples, the one or more see through displays can include one or more transparent carrier layers, and each of the transparent carrier layers can include one or more active optical elements. The light control device can also include an electrical component coupled to each of the transparent carrier layers.

The electrical component can direct an electrical current through each of the transparent carrier layers, and the directed electrical current can electrify the one or more active optical elements to create and move the one or more apertures. In some instances, two or more of the transparent carrier layers can be vertically stacked in more than one plane, and the one or more active optical elements in each of the two or more transparent carrier layers can become less transparent than the aperture when electrified. The one or more apertures can be defined by at least one of: (i) an area without the one or more active optical elements surrounded by an area in each transparent carrier layer with the one or more active optical elements; or (ii) an area without activation of the one or more active optical elements surrounded by an area in each transparent carrier layer with activation of the one or more active optical elements. The spatial location of each of the one or more apertures in each carrier layer can be displaced relative to one another.

In additional examples, the light control device can be configured to move the one or more apertures by off-axis projection. Further, the light control device can be utilized to produce the regional variation of visual information and sampling of the ocular field of view for at least one of vision, screening, customization, calibration, vision measurement, or vision monitoring.

Further, in some examples, the regional variation of visual information and sampling of the ocular field of view can produce at least one of: (i) an improvement of vision in an eye or in both eyes of a subject; (ii) a stabilization of vision in the eye or in both of the eyes of the subject. (iii) a correction of an ophthalmic or neurologic condition; (iv) an amelioration of a visual symptom in the eye or in both of the eyes of the subject with an ophthalmic or neurologic condition, disease, injury or disorder; (v) a reduction of a rate of vision loss in the eye or in both of the eyes of the subject with a vision loss from an ophthalmic or neurologic condition, disease, injury or disorder; (vi) a reduction of a rate of progression of an ophthalmic or neurologic condition, disease or disorder in the eye or in both of the eyes of the subject with an ophthalmic or neurologic condition, disease or disorder; (vii) a vision measurement or monitoring of the eye or both of the eyes of the subject.

The light control device also can include one or more cameras and at least one processor functionally coupled to the one or more cameras. The at least one processor can be configured to execute software instructions to capture light from at least one of peripheral to, above, below or behind an eye, a fellow eye, or both eyes of a subject, and deliver the light to the retina of the eye, the fellow eye, or both eyes of the subject.

Further, the light control device also can include one or more microphones and at least one processor coupled to the one or more microphones. The at least one processor can be configured to execute software instructions to convert an audible speech to a text in a preferred language and to display the text within a field of view of a subject. In some examples, the light control device also can include one or more light emitting diodes placed around the perimeter of the field of view, and the processor can be further configured to execute the software instructions to energize selectively the one or more light emitting diodes to indicate a direction from which the audible speech is produced.

In further examples, a method includes utilizing a light control device. The device is configured to move optically one or more apertures anterior to a retina of an eye between one or more positions anterior to the retina that are non-coaxial with a center of a pupil and a position anterior to the retina that is coaxial with the center of the pupil. The one or more apertures are moved at a rate between 50 hertz and 50 kilohertz, and the light control device produces a regional variation of visual information and sampling (V-VIS) of an ocular field of view.

Additionally, in some examples, anterior to the retina can include one of extraocular, intracorneal or intraocular placement, and the light control device can be configured to electro-optically move one or more apertures through one or more see-through displays placed anterior to the retina to produce the regional variation of visual information and sampling of the ocular field of view for at least one of vision, screening, customization, calibration, vision measurement, or vision monitoring. The light control device can also be configured to produce at least one of an improvement of vision in an eye or both eyes of a subject, a stabilization of vision in the eye or in both of the eyes of the subject, a correction of an ophthalmic or neurologic condition, an amelioration of a visual symptom in the eye or both of the eyes of the subject with the ophthalmic or neurologic condition, a disease, an injury or a disorder, a reduction of a rate of vision loss in the eye or both of the eyes of the subject with vision loss from the ophthalmic or neurologic condition, disease, injury or disorder, a reduction of a rate of progression of the ophthalmic or neurologic condition, disease or disorder in the eye or both of the eyes of the subject with the ophthalmic or neurologic condition, disease, or disorder, a vision measurement of an eye or both eyes of a subject, or a vision monitoring of the eye or both of the eyes the a subject.

The method also can include utilizing the light control device to produce at least one of an augmented reality image, a virtual reality image, or a combination of an augmented and virtual reality images. In other examples, the method also can include treating an eye using the light control device, and at a time prior to the treatment, during the treatment, or after the treatment, administering at least one of a genetic, epigenetic, optogenetic, retinal replacement or stem cell therapy for treating an ophthalmic or neurologic condition, disease, injury or disorder.

In further examples, the method can include treating an eye using the light control device, and at a time prior to the treatment, during the treatment, or after the treatment, administering a therapeutically effective amount of an anti-angiogenesis agent administered via at least one of an intravitreal injection, orally, topically, intraretinally, via an implant or via iontophoresis, wherein the combination therapy is for treating or ameliorating a symptom of a neovascular ophthalmic condition, disease, injury or disorder.

The method also can include treating an eye using the light control device, and at a time prior to, during, or after the treatment using the light control device, administering, topically, intraretinally, via intravitreal injections, via implants, or via iontophoresis, and for treating an ophthalmic or neurologic condition, disease, injury or disorder a therapeutically effective amount of at least one of: (i) an intraocular pressure-lowering agent comprising a miotic, an alpha or alpha/beta adrenergic agonist, a beta-blocker, a Ca2+ channel blocker, a carbonic anhydrase inhibitor, a cholinesterase inhibitor, a prostaglandin agonist, a prostaglandin, a prostamide, or a cannabinoid; (ii) a retinal cell- or cortical cell-neuroprotective or neuroregenerative agent comprising a rho-kinase inhibitor, an adenosine receptor agonist, a glutamate antagonist, a neurotrophic factor, or a neurotrophic factor regulator; or (iii) a combination of the intraocular pressure-lowering agent and the retinal cell- or cortical cell-neuroprotective or neuroregenerative agent. The ophthalmic or neurologic condition, disease, injury or disorder can include a glaucoma, a macular degeneration, an optic nerve atrophy, an optic nerve injury, an autoimmune neuro-degenerative disorder, or a cerebrovascular accident.

In further examples, the light control device may include one or more layers disposed anterior to a retina of an eye. The one or more layers are placed extraocularly and include one or more apertures, and one or more motors control movement of the one or more layers with apertures in front of the eye. The movement of the one or more layers generates a moving aperture effect that samples and delivers to the retina environmental light from an ocular field of view at a sampling rate between 50 hertz and 50 kilohertz.

DETAILED DESCRIPTION

Figure 1:
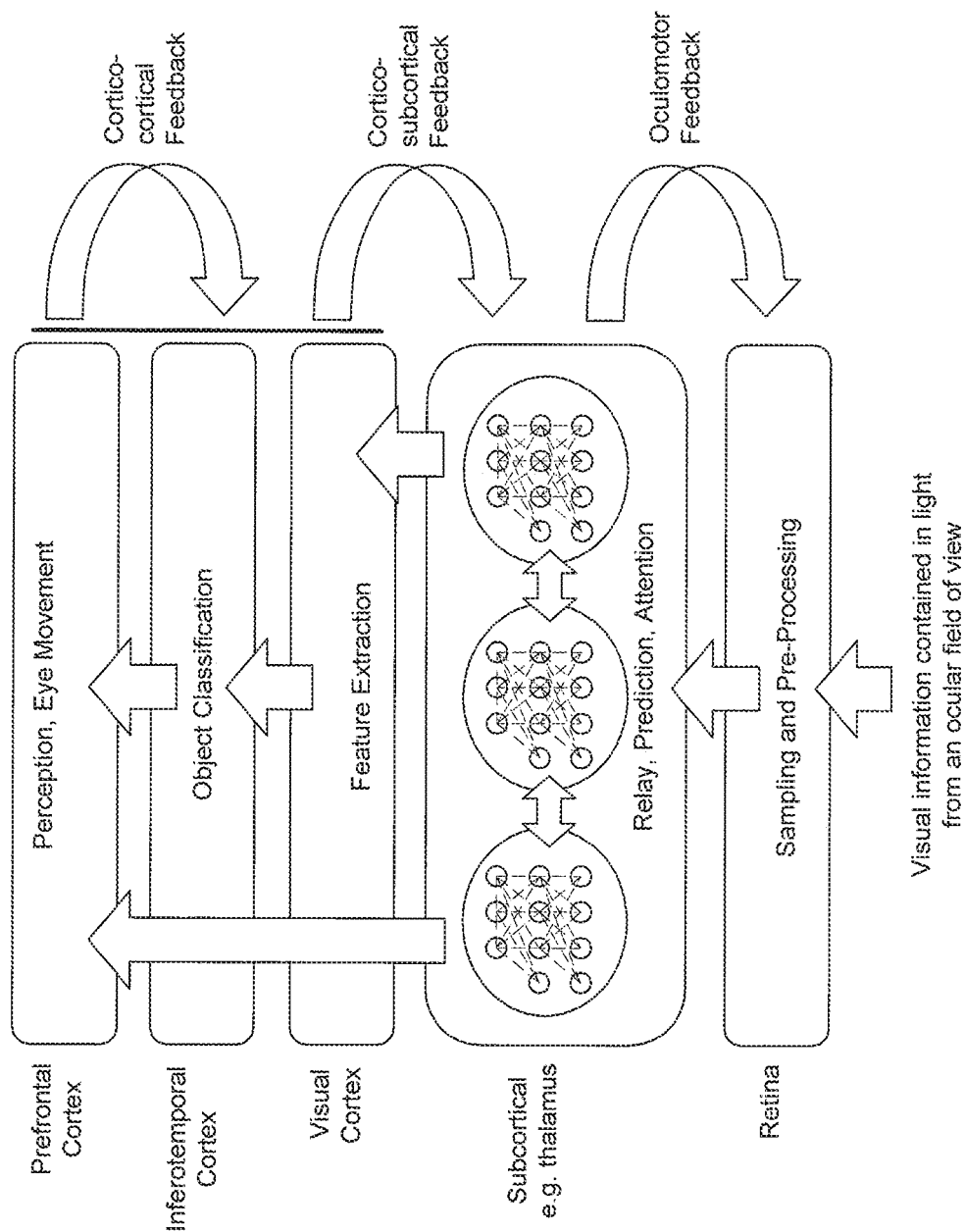
FIG. 1 is a flowchart showing the neural processing that results in visual perception, according to some examples.

Among those benefits and improvements that are disclosed herein, other objects and advantages of the exemplary embodiments can become apparent from the following description taken in conjunction with the accompanying figures. Detailed exemplary embodiments are disclosed herein; however, it is to be understood that these disclosed exemplary embodiments are merely illustrative and may be embodied in various forms. In addition, each of the examples given in connection with the various embodiments is intended to be illustrative, and not restrictive. Any alterations and further modifications of the features illustrated herein, and any additional applications of one or more of the principles illustrated herein, which can normally occur to one skilled in the relevant art and having possession of this disclosure, are to be considered within the scope of the disclosed exemplary embodiments. While the description herein teaches certain features as applied to various embodiments, it will be understood that various omissions, substitutions, and changes in the form and details of the device or method illustrated can be made without departing from the spirit of the disclosure. As will be recognized, certain of the exemplary embodiments described herein can be embodied within a form that does not provide all of the features and benefits set forth herein, as some features can be used or practiced separately from others. All changes which come within the meaning and range of equivalency of the claims are to be embraced within their scope.

Throughout the specification, the following terms take the meanings explicitly associated herein, unless the context clearly dictates otherwise. The phrases "In one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various of the exemplary embodiments may be readily combined, without departing from the scope or spirit of the exemplary embodiments.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

A. Introduction

The specification describes, among other things, exemplary devices and methods that perform a regional variation of visual information and sampling (e.g., V-VIS) of an ocular field of view by optically moving one or more apertures anterior to a retina between one or more positions anterior to the retina that are non-coaxial with a center of a pupil and a position anterior to the retina that is coaxial with the center of the pupil. The exemplary V-VIS devices described herein correspond to, and function as, light control devices that produce the regional variation of visual information and sampling. Further, and as described herein, "anterior to the retina" includes one of extraocular, intracorneal, or intraocular placement, and the one or more apertures are moved at a rate between 50 hertz and 50 kilohertz.

Certain of the exemplary V-VIS devices and methods can be utilized for at least one of screening for use of V-VIS, customization of V-VIS, calibration of V-VIS, V-VIS vision measurement, V-VIS vision monitoring, or any combination thereof. One or more of the exemplary V-VIS devices and methods can improve and/or stabilize vision in an eye or both eyes of a subject and/or correct an ophthalmic or neurologic condition. In some embodiments, the V-VIS delivery (e.g., using the exemplary V-VIS devices and methods described herein) of visual information from an ocular field of view to the retina also ameliorates a visual symptom or reduces the rate of vision loss or reduces the progression of vision loss or functionally measures vision, including but not limited to the visual processing effect of an ophthalmic or neurologic condition, disease, injury or disorder, or monitors vision.

Further, one or more of the exemplary V-VIS devices and methods described herein can provide a novel delivery of visual information from an ocular field of view to different areas of the retina at a rapid enough rate to overcome limitations of conventional light control devices, as well as limitations of natural visual processing and perception, to improve vision in subjects with decreased vision or an ophthalmic or neurologic condition or any combination thereof. In contrast to conventional devices and methods for delivering visual information from an ocular field of view to the retina, one or more of the exemplary V-VIS devices and methods can provide improved monocular and/or binocular visual outcomes and/or fewer visual adverse effects and/or more patient convenience and/or compliance with treatments for ophthalmic and/or neurologic conditions. In further contrast to some conventional devices, such as retinal prostheses, certain of the exemplary V-VIS devices and methods can be utilized with existing and/or natural neural circuitry in the retina and/or brain, do not require replacement of natural neural circuitry and do not interfere with normal natural vision processing mechanisms.

Examples of the V-VIS devices and methods described herein include extraocular devices, such as, but not limited to, spectacles, accessory devices for spectacles, heads up displays, visors, contact lenses, accessory devices for contact lenses, and viewing screens, such as, but not limited to, remotely accessible-televisions, -computers, and -mobile devices, corneal inlays, intraocular devices, intraocular lenses and intraocular lens accessories that are configured as V-VIS light control devices. The exemplary V-VIS devices and methods described herein can produce V-VIS in combination with augmented reality and/or virtual reality or can be part of an augmented and/or virtual reality system.

In some embodiments, one or more of the exemplary V-VIS devices and methods can be combined with other treatments for retinal and/or neurologic conditions, diseases, injuries and disorders including, but not limited to, genetic therapy, epigenetic therapy, optogenetic therapy, retinal replacement therapy, stem cell therapy and/or pharmacological agents, including but not limited to, anti-angiogenesis agents, intraocular pressure-lowering agents, neuroprotective agents and neuroregenerative agents.

The exemplary V-VIS devices and methods, as described herein, are configured to improve and/or stabilize vision in an eye or both eyes of a subject. Some embodiments of the exemplary devices and methods described herein correct an ophthalmic or neurologic condition. In some embodiments, the V-VIS delivery of visual information from an ocular field of view to the retina also ameliorates a visual symptom of an ophthalmic or neurologic condition, disease, injury or disorder, including, but not limited to, age-related macular degeneration (AMD), Stargardt's disease, Bests vitelliform macular dystrophy, a light-induced retinal injury, a cone dystrophy, reverse retinitis pigmentosa, myopic macular degeneration, a macular scar, an inherited retinal disorder, diabetic retinopathy (DR), a macular edema, a macular hole, a macular detachment, a macular pucker, a vascular retinal disorder (including, but not limited to, retinal vein occlusions and Coats' Disease), retinitis pigmentosa, a nutritional retinal disorder, an inflammatory retinal disorder, a glaucoma or other neuro-retinal or ganglion cell disorder, an autoimmune disorder (including but not limited to multiple sclerosis and lupus erythematosus), a cerebrovascular accident, dyslexia, amblyopia (caused by conditions including, but not limited to, a refractive error, medial opacity or obstruction, or an oculomotor condition, or any combination thereof), presbyopia and ametropia.

Some embodiments of the exemplary devices and methods described herein reduce, compared to an untreated control group, the rate of vision loss in an eye or both eyes of a subject with a vision loss from an ophthalmic or neurologic condition, disease, injury or disorder. Some embodiments of the exemplary devices and methods described herein reduce, compared to an untreated control group, the progression of an ophthalmic or neurologic condition, disease, or disorder. Some embodiments of the exemplary devices and methods described herein measure or monitor vision, including, but not limited to, effects of ophthalmic or neurologic conditions, diseases or disorders on visual processing and/or aid screening of subjects for V-VIS and/or a customization of V-VIS and/or a calibration of V-VIS.

B. Exemplary Devices and Methods for Regional Variation of Visual Information and Sampling FIG. 1 diagrammatically shows an integration of the various components of a visual system, according to some examples. Light carrying visual information from an ocular field of view is directed through the eye and delivered to light sensitive retinal cells that absorb the light and start processing the visual information. The light sensitive retinal cells convert the light energy to signals that are sent to other retinal cells and the brain where further processing, including but not limited to, coding, filtering and integration, combined with feedforward and feedback loops within the retina and brain and to and from extraocular muscles, results in visual perception.

Some embodiments of the exemplary V-VIS devices and methods of described herein produce novel delivery of light to the retina. Some embodiments of the exemplary devices and methods produce variations of sampling of light within an ocular field of view. In some exemplary embodiments, the movement of one or more apertures anterior to a retina between one or more positions anterior to the retina that are non-coaxial with a center of a pupil and a position anterior to the retina that is coaxial with the center of the pupil vary regionally the ocular field of view and/or the retinal area (or areas) to which an ocular field of view is presented. In some exemplary embodiments, the regional variation of the ocular field of view and/or the retinal area/s to which an ocular field of view is delivered by the one or more of the exemplary V-VIS devices and methods is determined by at least one of the following: the diameter of the one or more apertures, the transparency of the one or more apertures to selective wavelengths, the number of apertures, the diameter of the area within which the one or more apertures are moved, the positions to which the apertures are moved, the order in which the apertures are moved to different positions, the transparency to selective wavelengths of the area or portions of the area outside the one or more apertures and the rate between 50 hertz and 50 kilohertz at which the one or more apertures are moved.

In some exemplary embodiments, exemplary V-VIS devices and methods move one or more apertures that are substantially circular or hexagonal or elliptical or oval or square or rectangular or of any desired shape or any combination thereof. In some embodiments, exemplary V-VIS devices and methods move one or more apertures that are configured to have a constant or adjustable diameter, and/or greatest diameter, ranging from 0.1 mm to 4 mm. In some embodiments, exemplary V-VIS devices are configured to move one or more apertures within an area having a constant or adjustable diameter, and/or greatest diameter, ranging from 0.2 mm to 10 mm. In some embodiments, exemplary V-VIS devices and methods move one or more apertures that are configured to have a constant or adjustable diameter, and/or greatest diameter, ranging from 0.1 mm to 20 mm. In some embodiments, exemplary V-VIS devices are also configured to move one or more apertures within an area having a constant or adjustable diameter, and/or greatest diameter, ranging from 0.1 mm to 20 mm. In some embodiments, exemplary V-VIS devices and methods are configured to move the one or more apertures to positions that are partially overlapped, not overlapped or any combination thereof. In some embodiments, the positions to which the apertures are moved overlap areas outside the pupil under photopic or mesopic or scotopic illumination conditions or any combination thereof. In some embodiments, under low light illumination conditions, such as mesopic and/or scotopic conditions, electronic illumination enhancement methods known to those skilled in the art are employed. Some embodiments of the exemplary V-VIS devices are configured to move each of the one or more apertures in a pre-determined order, including, but not limited to, alternately, randomly, sequentially through all positions, in any other desired order or in any combination thereof.

In some embodiments, the exemplary V-VIS devices and systems deliver light with visual information from an ocular field of view to retinal cells with a duration of presentation, herein called a V-VIS sampling interval ("SI"), through each of the one or more apertures that is of sufficient duration to enable perception of the ocular field of view after further processing in the retina and brain. In some embodiments, V-VIS is accomplished by changing the position of one or more apertures at a rate between 50 hertz and 50 kilohertz, and not allowing the aperture to persist in any one position for more than one V-VIS SI. In some embodiments of the exemplary V-VIS devices and methods described herein, the SI is a time interval lasting between 0.02 ms and 20 ms.

The V-VIS sampling rate ("SR") of the one or more apertures is defined herein as the number of times per second that each SI is completed, i.e., the number of times per second that each aperture or one or more apertures are moved to each of the selected positions. In some embodiments, the SR is a rate between 50 hertz and 50 kilohertz. A V-VIS sampling cycle ("SC") is defined herein as the sequence of aperture positions. In some embodiments, the V-VIS sampling cycle includes some selected positions, to which each aperture or one or more apertures are moved more than one time during the sampling cycle.

In some embodiments, described herein, the exemplary V-VIS methods and devices are configured to produce an SR or variable SRs based on the speed of fixational eye movements, including, but not limited to, microsaccades, drifts and tremor. The speed of fixational eye movements often is modified by ophthalmic and/or neurological conditions, diseases, injuries or disorders.

In some embodiments, the exemplary V-VIS devices and methods and devices move the one or more apertures at an SR rate that is sufficiently rapid to enable stable perception. In some embodiments of the exemplary V-VIS methods and devices deliver light with visual information from an ocular field of view to retinal cells with a duration of presentation customized for an eye or both eyes of a subject. In some embodiments, the exemplary V-VIS devices and methods and devices move the one or more apertures at different rates for different eyes and/or subjects to enable stable perception without the perception of flicker by the subject. In some, the exemplary V-VIS devices and methods and devices move the one or more apertures at different rates for different eyes and/or subjects to enable stable perception without stroboscopic and/or phantom array effects. In some embodiments, the exemplary V-VIS devices and methods and devices move the one or more apertures at different rates for different eyes and/or subjects to enable stable perception without triggering adverse effects, including, but not limited to, headaches, migraines, cognitive defects and/or photosensitive epilepsy.

In some embodiments, the exemplary V-VIS devices and methods and devices move the one or more apertures at different rates for different eyes and/or subjects, depending on age and/or type and/or severity of an ophthalmic and/or neurologic condition, disease, injury or disorder and/or other factors. In some embodiments, a delivery of light by the exemplary V-VIS methods and devices is configured to be adjustable. In some embodiments, the exemplary V-VIS methods and devices deliver light with visual information from an ocular field of view to retinal cells with a duration of presentation through each of the one or more apertures that initially is too rapid to enable visual perception by an eye and/or both eyes of a subject, but is configured to allow adjustability of the SR, so that, upon slowing of the SR, the SR at which visual perception first becomes possible can be determined for a given eye and/or both eyes of a subject and depends upon various factors, including but not limited to, age and type or stage of infirmity of a subject. In some embodiments, the exemplary V-VIS methods and devices are configured for calibration of V-VIS treatment and staging of an eye and/or both eyes of a subject with an ophthalmic or neurological condition, disease, injury or disorder. In some embodiments, the exemplary V-VIS methods and devices are configured to monitor improvement in an eye and/or both eyes with an ophthalmic or neurologic condition, disease, injury or disorder after V-VIS treatment or after conventional therapy or after a combination thereof. For example, in some embodiments, the average SR required for visual perception in eyes with a certain condition, disease, injury or disorder is slower than the average SR required for visual perception in matched control eyes without that condition, disease, injury or disorder and increases with visual improvement after V-VIS therapy or after other therapy or after a combination thereof.

In some embodiments, the V-VIS devices and methods can be combined with a method or device for visual testing known to those skilled in the art of visual testing including, but not limited to, visual acuity testing, contrast sensitivity testing or perimetry, to distinguish vision problems caused by visually significant defocus of light at the retina from vision problems due to other causes, including, but not limited to functional or structural causes. Vision problems related to retinal defocus and/or refractive and/or accommodative errors are corrected and/or diminished with utilization of some embodiments of the exemplary V-VIS methods and devices described herein at a speed within a range of speeds that are normal for subjects with refractive errors and/or accommodative errors but without other ophthalmic or neurologic conditions, diseases, injuries or disorders. In some embodiments, the exemplary V-VIS methods or devices can be combined with a visual acuity testing method or device known to those skilled in the art of visual testing and including, but not limited to, visual acuity testing, contrast sensitivity testing or perimetry, to quantify and/or monitor over time the severity of vision impairment caused by defects in visual processing in the retina or brain in eyes. Vision impairment related to defects in visual processing in the retina and/or brain are corrected and/or diminished with utilization of some embodiments of the exemplary V-VIS devices and methods described herein, e.g., as applied to subjects at a speed within a range of speeds different from that applied to other subjects without defects in visual processing in the retina and/or brain. Methods described herein include V-VIS in combination with other medical or surgical treatments.

Some embodiments of the exemplary V-VIS methods and devices, as described herein, are configured to deliver light to the retina with less myopic and/or hyperopic vergence at the retina. Some embodiments of the exemplary V-VIS methods and devices are configured to deliver approximately collimated light through one or more moving apertures. Some embodiments of the exemplary V-VIS methods and devices move one or more apertures with diameters that are effective in reducing refractive errors in an eye of a subject with ametropia. Some embodiments of the exemplary V-VIS methods and devices move one or more apertures with diameters that are effective in increasing depth of focus in an eye of a subject with presbyopia. Some embodiments of the exemplary V-VIS methods and devices decrease refractive errors or increase depth of focus or any combination thereof, thereby decreasing symptoms of ametropia or presbyopia or any combination thereof. Some embodiments of the exemplary V-VIS methods and devices overcome limitations of conventional devices incorporating a small stationary aperture, including, but not limited to, visual field restriction, reduction of the amount of light reaching the retina, contrast sensitivity loss, reduction of stereopsis and diffraction blurring. Stationary apertures, if sufficiently small to collimate light and placed in front of a retina, restrict peripheral light rays from being delivered to the retina. In eyes with retinal macular lesions, a stationary small aperture often does not improve visual acuity and often causes a reduction in visual acuity by restricting light to dysfunctional areas of the retina. Stationary small apertures reduce total illumination and cause less light to reach the retina, thereby reducing visual acuity under low illumination conditions. Stationary small apertures in only one eye of a subject induce anisocoria and produce detrimental interocular differences in visual latency causing hazardous distortions of relative movement. Some embodiments of the exemplary V-VIS devices and systems, as described herein, overcome the limitations of a stationary small aperture through strategic and novel positioning and movement at between 50 hertz and 50 kilohertz of one or more apertures, thereby providing better illumination and better vision in an eye with an ophthalmic or neurologic condition, disease, injury or disorder than conventional devices with stationary small apertures.

In some embodiments of the exemplary V-VIS devices and systems, as described herein, the transparency of the one or more apertures to select wavelengths is constant or adjustable. In some embodiments, the transparency to select wavelengths of the area outside of the area within which the one or more apertures are moved is constant or adjustable.

In some instances, a range of wavelengths of light stimulates each type of retinal receptor to varying degrees. Yellowish-green light stimulates both L and M cones equally strongly, but only stimulates S-cones weakly. Red light stimulates L cones much more than M cones, and Scones hardly at all. Blue-green light stimulates M cones more than L cones, and Scones a bit more strongly, and is also the peak stimulant for rod cells. Blue light stimulates Scones more strongly and L and M cones more weakly than red or green light. The brain combines the information from each type of receptor to give rise to different perceptions of different wavelengths of light. Some embodiments of the exemplary V-VIS methods and devices alter a transparency to select wavelengths of the one or more apertures and/or of the area outside of the area within which the one or more apertures are moved to change the amount of stimulation of different types of retinal photoreceptors in an eye or both eyes of a subject for beneficial effects.

Some embodiments of the exemplary V-VIS methods and devices selectively alter the transparency of the one or more apertures and/or of the area outside of the area within which the one or more apertures are moved to wavelengths in the visible spectrum, which ranges from about 400 nm to 700 nm. Further, in some instances, chromatic dispersion may cause wavelengths in the visible spectrum to have a range of focus of about 2.25 diopters. Indices of refraction vary inversely with wavelength; blue rays (short wavelength) are refracted more than red rays (long wavelength). Some embodiments of the exemplary V-VIS methods and devices selectively alter a transparency to visible wavelengths of the one or more apertures and/or of the area outside of the area within which the one or more apertures are moved to change the defocus on the retina in an eye or both eyes of a subject. In some embodiments, the transparency to visible wavelengths of the one or more apertures may be altered using polarizing filters.

In some embodiments, the exemplary V-VIS methods and devices described herein can be configured to deliver light to the retina with less myopic and/or hyperopic vergence at the retina in different areas of the retina to effectively alter the emmetropization process and/or refractive development of an eye. In some embodiments of the exemplary V-VIS devices and methods can be configured to reduce defocus on a retinal area within the central retina or outside of the central retina or any combination thereof to reduce, compared to an untreated control group, the rate of progression of ametropia, including but not limited to myopia, wherein the central retina is centered on the foveola, may contain the fovea or parafovea or macula or any combination thereof and may be of any diameter between 1.5 and 6 mm. In some embodiments, the exemplary V-VIS methods and devices described herein can be configured to reduce defocus in retinal areas by the diameter, location, chromaticity or any combination thereof of one or more of the moving apertures, of one or more areas without moving apertures or of any combination thereof.

One or more of the exemplary V-VIS devices and methods, as described herein, can be configured to improve and/or stabilize vision in an eye or both eyes of a subject. The vision improvement and/or stabilization includes, but is not limited to, improvements and/or stabilization of at least one of the following of visual acuity (including at least one of uncorrected and best spectacle-corrected visual acuity for distance, intermediate and near visual acuity), hyperacuity, stereoacuity, vernier acuity, contrast sensitivity, depth of focus, color vision, visual fields, peripheral vision, night vision, face recognition, light adaptation, dark adaptation, vision-related quality of life, or any combination thereof.

Further, some embodiments of the exemplary V-VIS devices and methods, as described herein, improve vision by altering visual processing, including, but not limited to, neural coding and/or integration and/or filtering and/or neuroadaptation and/or perception of an ocular field of view. Some embodiments of the exemplary V-VIS devices and methods produce a novel delivery of light to retinal cells to cause at least one of the following: (i) alteration of sampling of visual information to enable more correct retinal visual information to be encoded by functional retinal cells in multiple retinal areas and transmitted with improved adaptive and/or predictive sensitization and/or integration from the retina to the brain; (ii) increase in effective and/or spontaneous searching for integration of more visual information; (iii) minimization of the effects of fixation instability and/or defective gaze selection (iv) beneficial alteration of neural attentional modulation; (v) beneficial alteration of the excitatory/inhibitory balance of the visual systems in both eyes and in the brain, including but not limited to altering converging excitatory and inhibitory inputs in one or more visual pathways; (vi) beneficial activation of previously unutilized or underutilized sensory, motor, and cognitive systems in the eye and brain; and (vii) beneficial neural adaptation using residual oculomotor and/or sensory plasticity. In some embodiments, the exemplary V-VIS devices and methods described herein can improve a functioning of retinal circuitry, including, but not limited to connectivity functions in visual processing involving photoreceptors and/or ganglion cells and/or amacrine cells and/or bipolar cells and/or horizontal cells and/or Muller cells or any combination thereof. In some embodiments, the exemplary V-VIS devices and methods can improve and/or trigger certain processes of neural adaptation, including but not limited to, use of alternate, latent, and/or new natural visual pathways in the retina and brain. Some embodiments of the exemplary V-VIS devices and methods can improve visual processing and/or perception without requiring replacement of existing and/or natural neural circuitry in the retina and/or brain and without interfering with normal natural vision processing mechanisms.

Some embodiments of the exemplary V-VIS devices and methods may produce a regional variation of visual information and sampling in combination with augmented reality and/or virtual reality, or may be implemented as a part or a component of an augmented and/or virtual reality system. Some embodiments of the exemplary V-VIS devices and methods, as described herein, can produce regional variations of visual information and sampling in conjunction with at least one of an augmented reality image, a virtual reality image, or any combination thereof to improve and/or stabilize and/or restore vision. Some embodiments of the exemplary V-VIS devices and methods described herein combine the novel V-VIS delivery to the retina with presentation to the retina of certain video, graphical and/or chromatic and/or achromatic additions, deletions, and/or attenuations of light with varying spatial, temporal and/or brightness patterns that are superimposed over the view of a natural scene. Some embodiments of the exemplary V-VIS devices and methods produce multiple regional variations of chromatic and/or achromatic spatial and/or temporal and/or contrast information of light within an ocular field of view before delivery to retinal cells by regional chromatic and/or achromatic highlighting and/or filtering and/or blocking. Some embodiments of the exemplary V-VIS devices and methods provide regional visual chromatic and/or achromatic excitatory and/or inhibitory stimuli to one or both eyes while a subject is viewing a natural visual scene within the ocular field of view during normal daily activities, in order to improve vision and/or restore vision in a subject with low vision or vision loss from a condition, disease, injury or disorder. Some embodiments of the exemplary V-VIS devices and methods, as described herein, can produce regional variations of visual information and sampling in conjunction with at least one augmented reality image or at least one virtual reality image (or any combination thereof) to alter and/or improve neural coding, filtering, integration and/or adaptation in the retina and/or brain, resulting in more complete and/or correct perception of a natural visual scene.

In some embodiments of the exemplary V-VIS methods and devices, a delivery of light to retinal cells through the one or more moving apertures decreases cumulative exposure to light over time of retinal cells receiving light during only a portion of each sampling cycle of the one or more apertures, when compared to retinal cells receiving light during a longer portion of the sampling cycle or during the entire sampling cycle or in eyes without a delivery of light by one or more of the exemplary V-VIS devices and methods described herein.

In some embodiments of the exemplary V-VIS methods and devices, the delivery of light decreases cumulative exposure to select wavelengths of light over time by selective wavelength attenuation to retinal cells receiving light through the one or more moving apertures and/or to retinal cells outside the area within which one or more apertures are moving. In some embodiments, as described herein, one or more of the exemplary V-VIS devices are configured to block selective wavelengths, including, but not limited to, UV wavelengths or blue or blue and violet wavelengths between 415 and 455 nm or other predetermined wavelengths or any combination thereof, which are delivered to the retina through one or more of the moving apertures or through an area without moving apertures or through any combination thereof during photopic or mesopic or scotopic illumination conditions or any combination thereof.

In some embodiments of the exemplary V-VIS devices and methods, the decreased cumulative exposure over time of retinal cells to light, with or without selective wavelength attenuation, reduces photostress and/or metabolic stress and/or phototoxicity in retinal cells. In some embodiments of the exemplary V-VIS devices and methods, the decreased cumulative exposure over time of retinal cells to light, with or without selective wavelength attenuation, can be continued for a period of time ranging from months to years. Decreased cumulative exposure to light over a period of time ranging from months to years of retinal cells in diseased retinas, including, but not limited to, retinas with age-related macular degeneration can prevent progression of retinal cell damage or drusen formation due to one or more of apoptosis, necrosis, pyroptosis and autophagy. In some embodiments of the exemplary V-VIS devices and methods, selective highlighting of light to viable retinal cells can increase their activation of repair and regenerative processes in damaged retinal areas, thereby also stimulating retinal repair and regenerative processes. In some embodiments of the exemplary V-VIS devices and methods, the regional variation of visual information and sampling, as described herein, can stimulate viable cells' triggering of cell repair, cell regeneration, or a combination thereof within damaged retinal cells or retinal areas.

Examples of the V-VIS devices described herein include, but are not limited to, extraocular devices, spectacles, spectacle accessories, contact lenses, contact lens accessories corneal inlays, intraocular devices, intraocular lenses and intraocular lens accessories that are configured, collectively or individually, as V-VIS light control devices. Some embodiments of the exemplary V-VIS light control devices and methods described herein can produce regional variations of visual information and sampling in combination with augmented reality and/or virtual reality, or can be part of or incorporated within an augmented and/or virtual reality system.

Some embodiments of the exemplary V-VIS devices and methods can perform operations that move one or more apertures electro-optically through one or more see-through displays placed anterior to the retina. For explanatory purposes, well-known features of optical technology have been omitted or simplified in order not to obscure the basic principles of the disclosed embodiments. In some embodiments, certain of the exemplary V-VIS devices are configured with components for see-through microdisplays that include, but are not limited to, at least one of a light source, optics, optomechanics, or visual system-optics interfaces.

Figure 2:
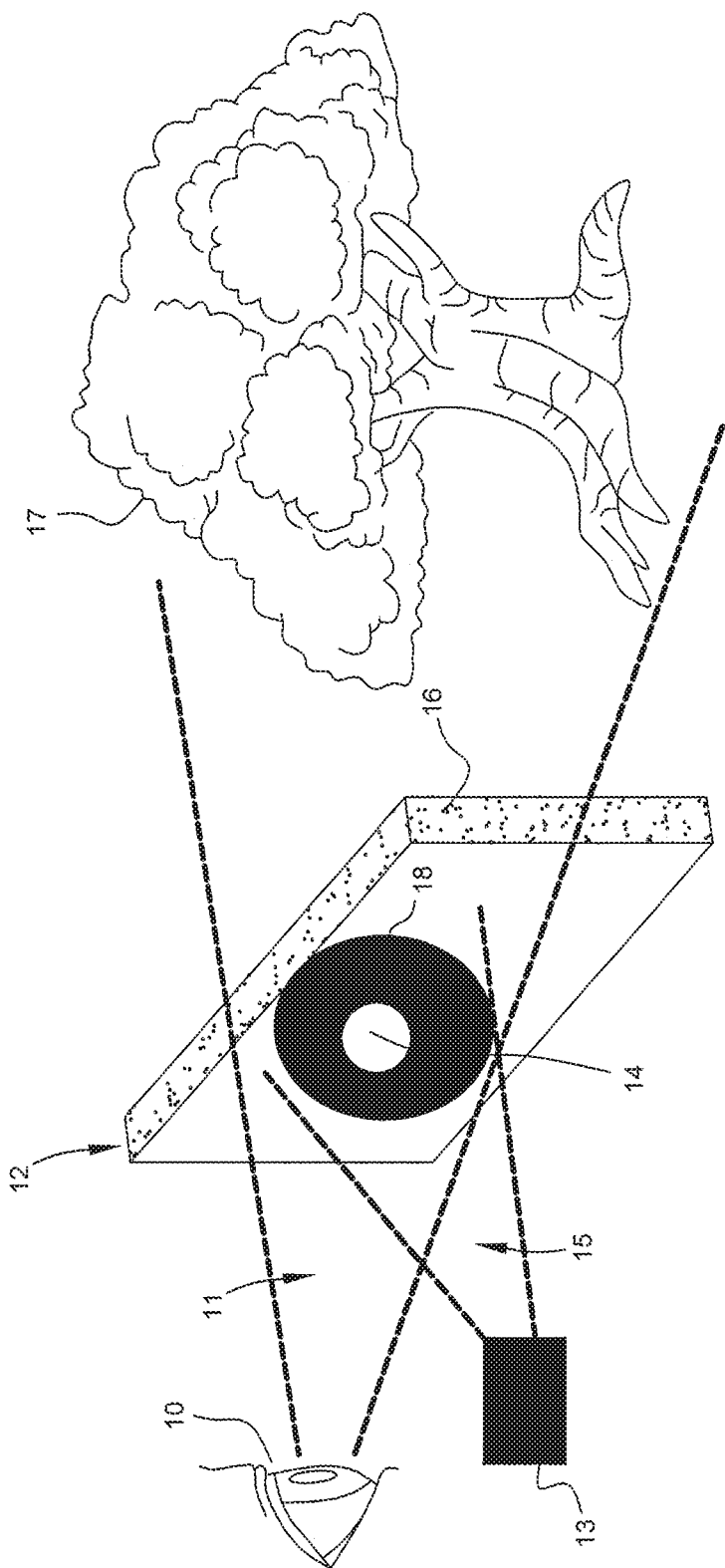
FIG. 2 illustrates an example of a light control device comprising a transparent reflective diffuser display upon which moving apertures can be formed by off-axis projection, according to some examples.

FIG. 2 illustrates an exemplary V-VIS light control device and method for creating a moving aperture, according to some examples. Referring to FIG. 2, a retina of a viewer's eye 10 observes an ocular field of view 11 through a transparent display 12. The transparent display can be one or more of a heads-up display, a visor, a head mounted display, a clip-on lens, and an eyeglass lens or eyeglass accessory device. While viewing a tree 17, for example, in the natural environment, areas of the viewer's retina are also exposed to a moving aperture 14 that is created on the surface or within the material of the transparent display, e.g., using off axis projection onto a transparent reflective diffuser display system or other transparent display containing or coated with light emitting particles 16 activated by a projector 13. The projector 13 emits excitation light 15, including but not limited to UV or IR light. Some wavelengths of light in the infrared region, for example, can be projected through the iris in an eye with a small pupil to reach a transparent display system having at least one layer of materials that respond to the projected light to form a moving aperture effect and other images or test messages. In some embodiments, the projected light energy may carry images and text directly to the retina.

In some examples, the projector 13 may be functionally coupled to a controller (not illustrated in FIG. 2). The controller may include one or more processors that, upon execution of software instructions (e.g., locally stored by the controller within a tangible, non-transitory memory or included within a received signal), causes the controller to generate and transmit a control signal to the projector 13. Based on the received control signal, projector 13 may selectively emit and project excitation light 15 onto the transparent reflective diffuser display system or the other transparent display, as described above.

UV sources include, but are not limited to, solid state lasers, semiconductor laser diodes, gas lasers, dye lasers, excimer lasers, and other appropriate UV light sources. The IR lasers include, but are not limited to, solid-state lasers, semiconductor laser diodes and other appropriate IR sources.

Excitation beam intensities from the light source can be modulated to yield visible fluorescence of varying chromaticity, intensity or gray scales. The excitation light is absorbed by light emitting particles that emit visible light to the retina of the viewer's eye. The intensity and placement of the output of one or more projectors, e.g., projector 13, is modulated to create one or more moving apertures to appear in the field of view.

The light emitting particles 16 incorporated into the transparent display 12 may be chromatic or achromatic. Light emitting particles may be nano-particles or molecules, and thus smaller than the wavelength of visible light in order to eliminate light scattering and when activated, produce the less transparent to opaque area 18 ranging from 0.2 mm to 10 mm in diameter, surrounding and defining a transparent aperture 14 having a diameter ranging from 0.1 mm to 4 mm.

FIGS. 3A-3B, 4A-4D, and 5 illustrate additional exemplary embodiments of devices and methods for delivering visual information from an ocular field of view to a retina using regional variation of the visual information to control sampling of the visual information by the retinal cells of an eye. This variation of visual information and sampling (e.g., V-VIS) is accomplished with the one or more of the devices and methods illustrated in the following figures, but should not be restricted to or limited in scope to the embodiments shown.

Figure 3A:
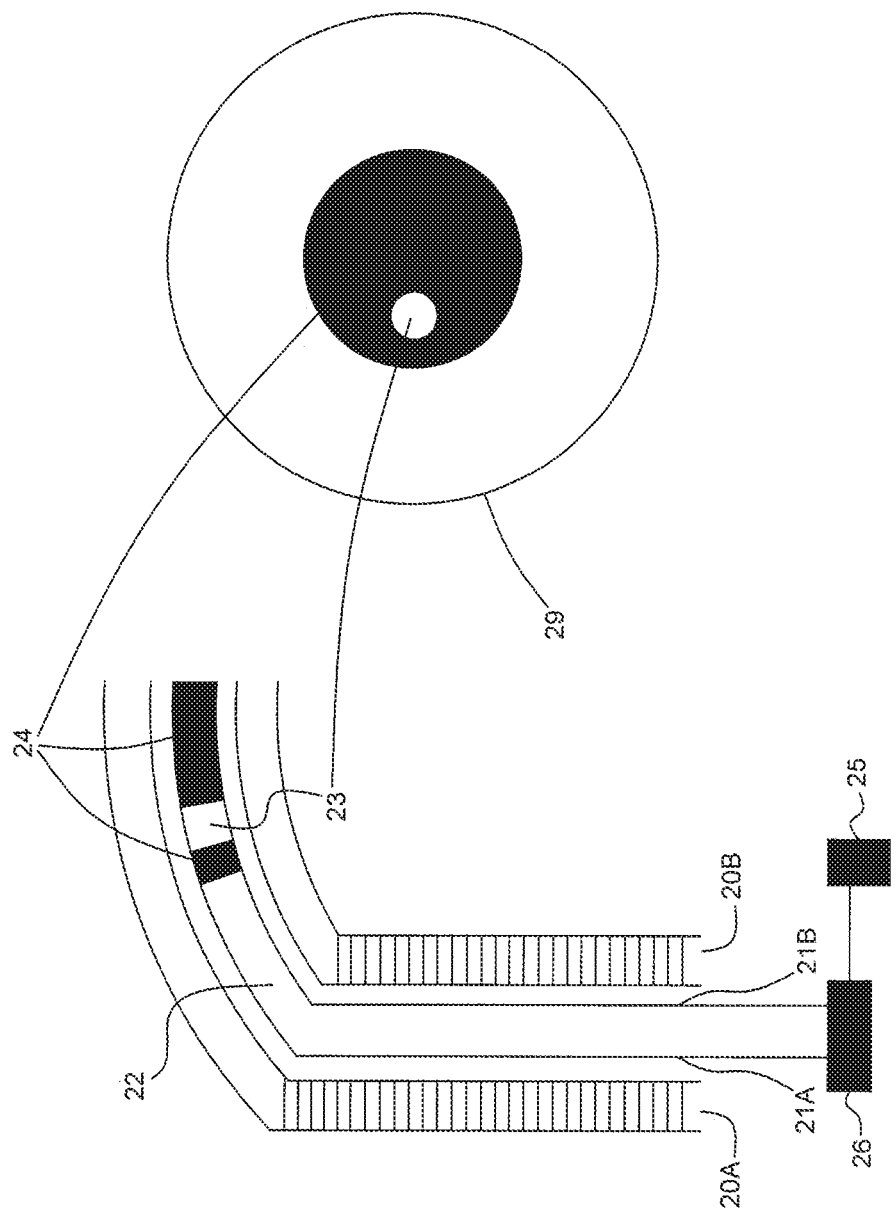
FIG. 3A is a diagram of a light control device, comprising a substantially transparent liquid crystal or other optically activated material contained in a thin film defined herein as a carrier layer or carrier layer unit, showing a moving aperture at a single position during a single sampling time interval, according to some examples.

FIG. 3A illustrates a partial cross section view and top view of a basic component, defined herein as a carrier layer unit, of an exemplary V-VIS device. A partial cross-section of the exemplary V-VIS device is shown in which two transparent layers 20A and 20B create a space 22 which is partially filled with one or more active optical elements 24. In some examples, transparent layers 20A and 20B can be flat or curved and composed of glass or plastic, and can include, but are not limited to polysulphones, polyetherimides, and/or other thermo-plastic materials having a refractive index of approximately 1.67 and thus no optical power. Further, the one or more active optical elements 24 be formed from a material having a refractive index of approximately 1.67, such as, but not limited to, one of polymer light emitting diodes (PLED), bi-stable liquid crystals, surface stabilized ferroelectric liquid crystals (SSFLF), transparent and color-tunable organic light-emitting diodes (OLEDs), ferroelectric liquid crystal, super-twisted liquid crystal, or a liquid crystal voltaic material.

The inside surface of each of transparent outer layers 20A and B, which faces the space 22, is lined with an optically transparent electrically conductive layer 21A and 21B made of a conductive material, such as, but not limited to, an indium tin oxide (ITO), a conductive organic material, such as poly(3,4-ethylenedioxythiophene) poly(styrene-sulfonate), and/or carbon nano-tubes. Further, the conductive material may also include traces of metals such, as silver or aluminum for increasing conductivity. The conductive layers 21A and 21B can be connected to a power 25 and drive box 26, which may be housed in one unit or divided into multiple units, and which may have an on/off switch, power supply and drive software to apply a desired voltage through one or more areas of the conductive layer to the active optical material 24 which then changes its optical properties from transparent to varying degrees of opacity in response to the voltage. Multiple variations in the color, and locations and size of areas of opacity and transparency can be achieved by configuring some embodiments of the exemplary V-VIS devices with different patterns and densities of active optical material within the space 22 between the transparent outer layers 20 A, B of the carrier layer and/or by configuring the pattern of electrical stimulation via the conductive layer.

In some embodiments of the exemplary V-VIS devices and methods, the carrier layer can incorporate optical filters that block specific ranges of harmful wavelengths of light, including but not limited to blue and violet wavelengths between 415 and 455 nm and/or UV wavelengths for prevention of retinal photo-damage.

In some embodiments of the exemplary V-VIS devices, the carrier layer incorporates a broad band anti-reflective (AR) coating that is applied to the carrier layer to minimize ghosting. The AR coating can be either a single layer MgF2 or a multilayer coating. Multilayer coatings of a variety of materials and a variety of absolute and relative thicknesses can be used to achieve the AR function.

In some embodiments of the exemplary V-VIS methods and devices described herein, each carrier layer unit has an arrangement of active optical material 24 surrounding an area 23 devoid of the active optical material. The aperture of these exemplary V-VIS devices and methods may, in some embodiments, be defined by an area without one or more active optical elements surrounded by an area in each carrier layer with the one or more active optical elements (e.g., the one or more active optical elements within each carrier layer become less transparent than the area of the aperture when electrified). The aperture can be configured with a diameter ranging from 0.1 mm to 4 mm, while the surrounding area is configured to have a diameter ranging from 0.2 mm to 10 mm. The degree of opacity of the aperture and/or surrounding area is determined by the density and placement of active optical material.

Multiple apertures can be formed within a single layer by virtue of where active optical material is placed within that layer. In some embodiments, the size, location and opacity of the aperture and/or surrounding area is determined by altering the pattern of electrical stimulation via the conductive layer (e.g., based on control signals generated by a controller having a processor that executes locally stored or received software instructions). In some embodiments, the one or more apertures in the carrier layer are defined as areas without activation of the one or more active optical elements surrounded by an area in the carrier layer characterized by activation of the one or more active optical elements. The position of the one or more apertures may be determined by a selective application of electrical energy to one, or more, of the carrier layers. The position of the one or more apertures changes at a rate of between 50 hertz and 50 kilohertz. One position of the one or more apertures is coaxial with the center of the pupil, while the one or more other positions of the one or more apertures are non-coaxial with the center of the pupil.

Figure 3B:
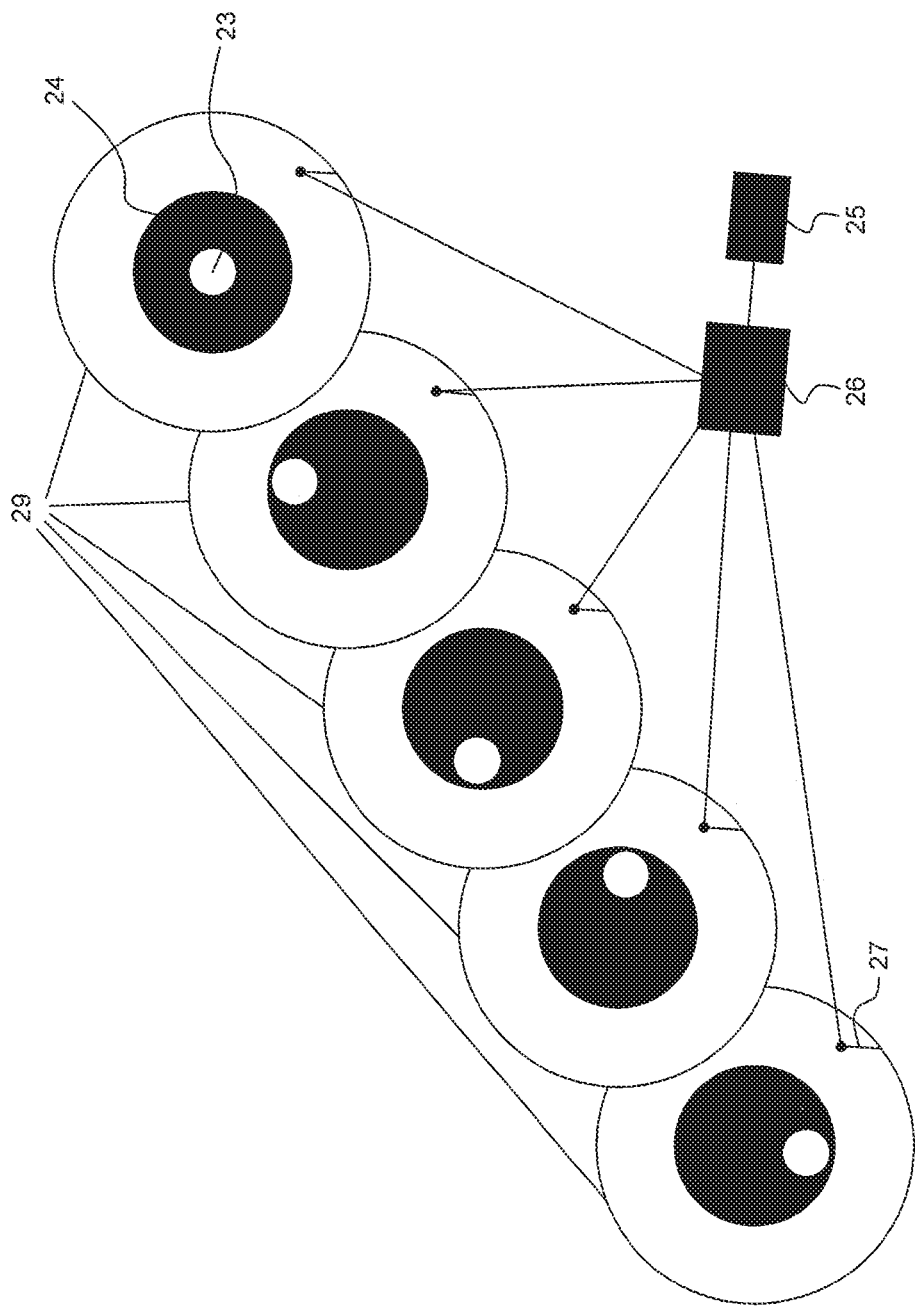
FIG. 3B is an illustration of a light control device comprising vertical stacking of multiple carrier layer units of FIG. 3A, each containing optically active material, and showing five possible aperture positions used to create a moving aperture effect in accordance with some examples.

FIG. 3B is an illustration of vertical stacking of multiple carrier layer units of FIG. 3A in order to create the moving aperture effect, according to some examples. A programmable controller 26 connected to a power source 25 sends electrical current either through a direct connection or remotely through a radio frequency antenna 27 to the active optical material 24 in each of the carrier layer units 29. In some examples, the programmable controller 26 may include one or more processors that, upon execution of software instructions (e.g., locally stored by the controller within a tangible, non-transitory memory or included within a received signal), causes the programmable controller 26 to route selectively the electrical current (e.g., as a control signal) to the active optical material 24 in each of the carrier layer units 29 using any of the processes described herein.

Each carrier layer unit has an arrangement of active optical material 24 surrounding an area 23 devoid of the active optical material. The aperture of the exemplary V-VIS devices and methods is created by the area without one or more active optical elements being surrounded by an area in each layer with one or more active optical elements; the one or more active optical elements within the carrier layer becomes less transparent than the area of the aperture when electrified, e.g., by the received electrical current. In some embodiments of the exemplary V-VIS devices, two or more transparent carrier layers are vertically stacked, such that the one or more active optical elements in each of the two or more transparent carrier layers becomes less transparent than the aperture when electrified.

In some examples, as described herein, the one or more apertures can be defined by at least one of an area without the one or more active optical elements being surrounded by an area in each carrier layer with the one or more active optical elements. In other examples, the one or more apertures can be defined by an area without activation of the one or more active optical elements surrounded by an area in each carrier layer with activation of the one or more active optical elements. In further examples, the spatial location of each of the one or more apertures in each carrier layer can be displaced relative to each of the other apertures in each carrier layer. In some embodiments the location and number of positions of the one or more apertures, the sequence of positions, and the interval between changes in positions may be customized for a specific person or a specific condition, disease, injury or disorder.

Figure 4A:
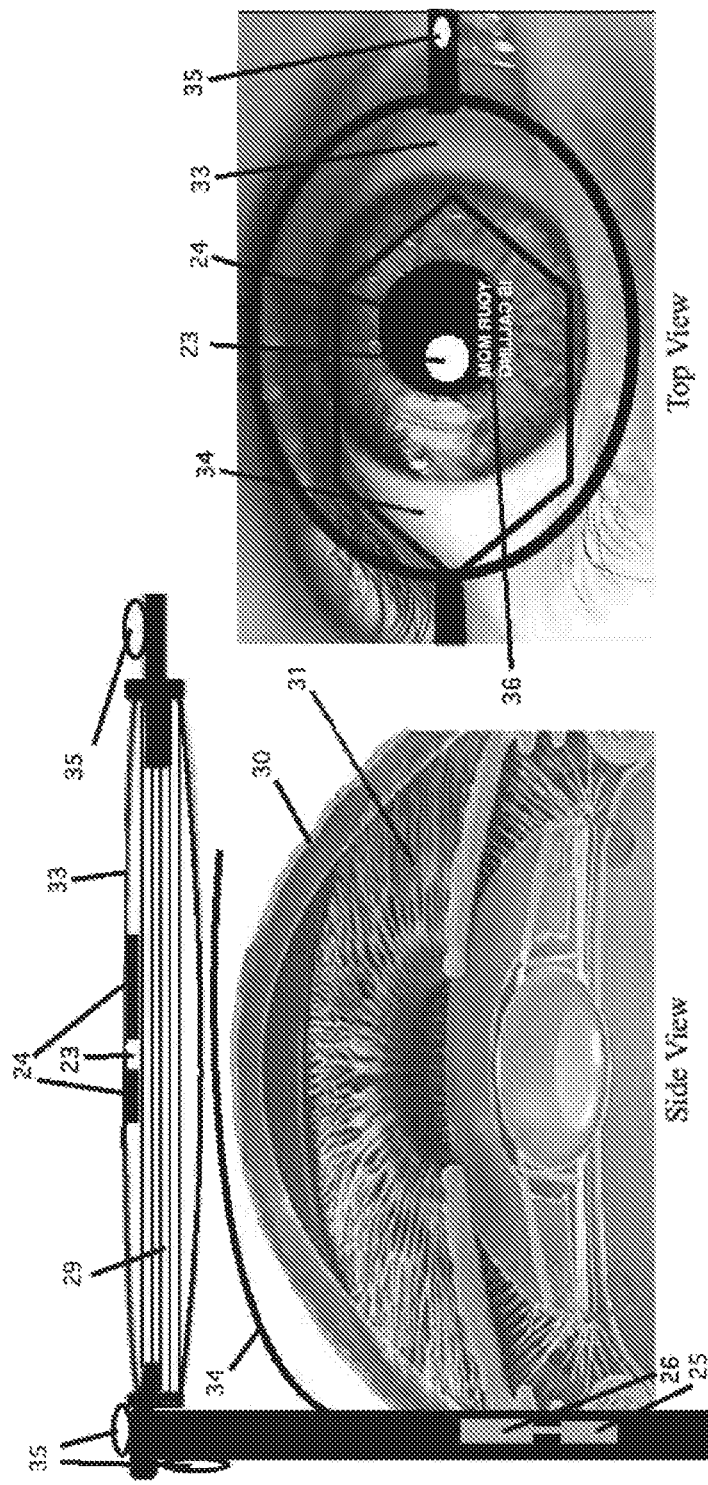
FIG. 4A is a side and top view of an eye showing the invented carrier layers of FIG. 3B within a light control device, comprising a pair of spectacles and a waveguide, and a moving aperture at one position during a single sampling time interval in accordance with some examples.

FIGS. 4A-4D depict a cross section of an eye showing various exemplary placement locations for a V-VIS device anterior to a retina of the eye. In FIG. 4A, the eye has a cornea 30 overlying the iris 31. In some examples, a V-VIS device, such as the exemplary V-VIS device illustrated in FIGS. 2 and 3, can be placed inside, or clipped to a spectacle lens 33 or placed in one or more waveguides 34 connected to an eyeglass frame 32. The frame 32 houses a power source 25 and programmable controller 26 which is connected to the one or more carrier layers 29 in or attached to the spectacle lens using an appropriate attachment method or mechanism. Each activated carrier layer produces one or more apertures 23 as described previously, e.g., based on electrical current selectively routed by the programmable controller 26 via the control signal. In some examples, the programmable controller 26 may receive input data, e.g., feedback from a sensor or a remotely accessible device (not illustrated in FIG. 4A), and may perform a calibration or configuration processes based on the received input.

FIG. 4A shows a single aperture in one position during a single sampling interval. The chosen position sequence of the moving aperture and SI determine the sampling of light by the retina. The exemplary V-VIS device of FIG. 4A can be configured to move optically an aperture anterior to a retina between one or more positions anterior to the retina that are non-coaxial with the center of the pupil and a position anterior to the retina that is coaxial with the center of the pupil.

The transparent waveguide 34 shown in FIG. 4A can, for example, act as a see-through display. In some embodiments, the exemplary V-VIS devices and methods described herein can include multiple waveguides arranged in at least one of vertically stacked in layers, adjacent to one another in a single layer, holographically multiplexed, or any combination thereof. Apertures and surrounding opaque areas such as those described in FIGS. 2, 3A and 3B, can be projected through the waveguides to the retina.

In some embodiments, the see-through display of the exemplary V-VIS devices and methods described herein can be further configured to display at least one augmented reality image, at least one virtual reality image, or any combination thereof. In one example, the programmable controller 26 may maintain local data characterizing the at least one virtual and/or augmented reality image within a tangible, non-transitory memory and, upon execution of software instructions, may generate a control signal that causes a V-VIS device to generate and display the at least one virtual and/or augmented reality image, e.g., on the transparent waveguide 34.

In other examples, the programmable controller 26 may be communicatively coupled to a virtual-reality or augmented-reality (VR/AR) system or device across one or more communications networks, such as a short-range communications network using Bluetooth™ communications protocols or near-field communications (NFC) protocols. The programmable controller 26 may receive data transmitted by the VRJAR system or device and responsive to the data, generate the control signal that causes the V-VIS device to generate and display the at least one virtual and/or augmented reality image, as described herein (not illustrated in FIG. 4A).

An exemplary embodiment of the use of augmented reality is in the case of a subject with loss of both vision and hearing, often co-morbidities in elderly patients, as well as in a number of inherited syndromes or disorders such as Alport, Usher, Marshall, Stickler, Duane, Leber, and Norrie and in infectious diseases such as Cytomegalovirus and Rubella. One or more of the exemplary V-VIS devices, as described herein, may be configured to combine vision improving moving apertures with multiple directional microphones 35 built into head-mounted or spectacle frames connected to the VRJAR system or device. In some examples, and upon execution of one or more application programs, the VRJAR system or device can perform operations that receive audio data captured by the one or more of the directional microphones 35. Based on the captured audio data, the VRJAR system or device can perform further operations that sense a source location of speech, convert the sensed speech to text of a preferred language, and display enlarged text (e.g., "Your mom is calling") 36 as an augmented reality image or layer on the waveguide 34 within the field of view of the sight- and hearing-impaired subject. Further, in some embodiments, added directional cues are given by means of one or more light emitting diodes placed around the perimeter of the field of view (e.g., around a perimeter of waveguide 34) to indicate to the hearing-impaired subject the direction from which the audible speech is produced. In some embodiments, one or more of the exemplary V-VIS devices described herein can include one or more microphones, and can include, or be in communication with, one or more processors or processing units that execute applications programs or software instructions that convert an audible speech to a text in a preferred language and to display the text within a field of view of a subject using the exemplary V-VIS devices. Further, and as described herein, one or more of the exemplary V-VIS device may further comprise one or more light emitting diodes placed around the perimeter of the field of view to indicate the direction from which the audible speech is produced. The application programs and the software instructions may include an Application Programming Interface (API) to create visual alerts for incoming texts and phone calls, as well as other alerts and notifications, and can convert speech from the telephone to viewable text.

In some embodiments, one or more of the exemplary V-VIS device can be combined with an eye tracking or gaze interactive assistive technology, examples of which include, but are not limited to, technologies available from Tobii Dynavox (Pittsburgh, Pa.) for subjects with speech and/or motor impairments. As the exemplary V-VIS devices and methods can improve a visually impaired subject's ability to see, eye tracking or gaze interactive assistive technology allows subjects who also have speech or motor disability to better focus their gaze on words, letters and commands, which results in improved eye tracking and infrared reflex readings from the corneal surface of their eyes, allowing them to communicate, regain personal independence, learn and interact with others and with computers, write emails, access social networking sites, acquire new skills and promote creativity, thereby increasing health and happiness.

In another exemplary embodiment, the head mounted or spectacle frames (e.g., as connected by Bluetooth™ to the processor described herein) can be combined with cameras directed peripherally in order to treat subjects with partial loss of the normal field of view, such as in, for example, subjects with hemianopsia, quadrantanopia or unilateral loss of temporal visual fields. Using AR techniques concurrent with the intermittent V-VIS display of the current field of view, light carrying information from the lost part of the total field of view is delivered to the remaining functional parts of the retina-brain complex for interpretation, integration and viewing. The intermittency of V-VIS prevents confusion and distraction that would result if the missing parts of the field of view were constantly displayed in a conventional picture-within-picture technique.

In some embodiments, one or more of the exemplary V-VIS devices can be combined with a concurrent display of augmented reality content (e.g., on a corresponding waveguide, etc.), wherein the use of augmented reality together with V-VIS captures light from a field of view larger than the field of view of a subject's eye, fellow eye or both eyes and delivers the light to the retina. The visual field of an eye normally extends more than 90° temporally, 60° nasally and superiorly, and about 70° inferiorly. In some embodiments, the exemplary V-VIS devices and methods described herein can expand the field of view of a subject's eye, fellow eye or both eyes for a total field of view that can be configured to be fixed or variable and to encompass any chosen number of degrees up to 360 degrees around the subject's eye, fellow eye or both eyes. In further embodiments, the exemplary processor described herein can be combined with cameras directed peripheral to and/or above and/or below and/or behind an eye, fellow eye or both eyes. In additional embodiments, the one or more of the V-VIS devices can be combined with a concurrent augmented reality display, wherein the use of augmented reality together with V-VIS captures light from a field of view larger than the field of view of a V-VIS device alone or an AR device alone to provide the subject with an expanded field of view. In some embodiments, the combination of the V-VIS and AR devices comprises 3D detection and/or high speed tracking.

In some embodiments of the devices and methods that are configured for the use of V-VIS combined with AR, light collimated by V-VIS apertures can be delivered to a retina from a field up to 360 degrees around an eye or both eyes of a subject. In some embodiments, one or more of the exemplary V-VIS devices can be further configured with one or more cameras and software to capture light from at least one of peripheral to, above, below and behind an eye, a fellow eye or both eyes of a subject and deliver the light to the retina of the eye, the fellow eye or both eyes of the subject.

Figure 4B:
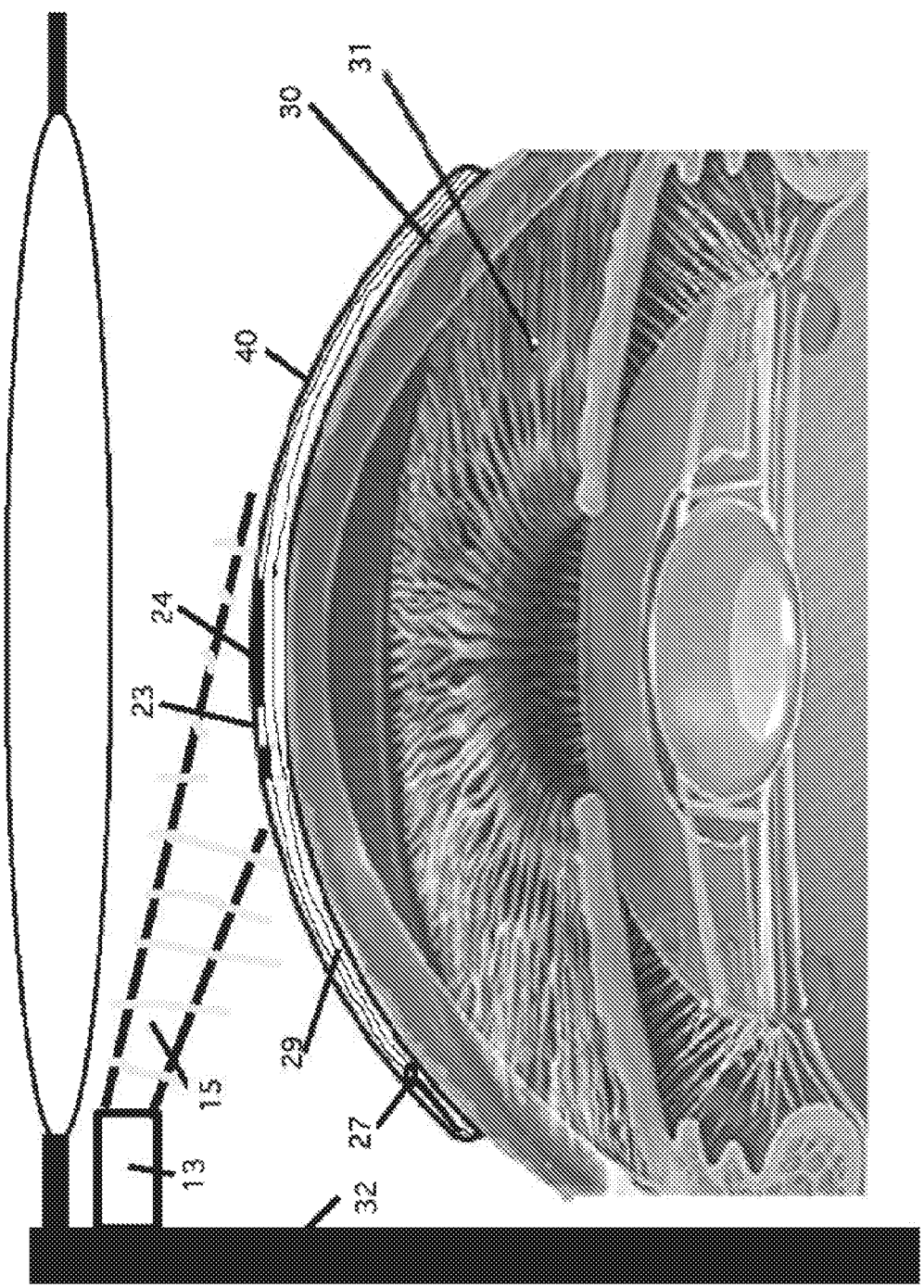
FIG. 4B is a side view of an eye with a light control device comprising a contact lens and an off-axis projection system of FIG. 2, creating a moving aperture herein depicted at one position during a single sampling time interval in accordance with some examples.

FIG. 4B shows two different embodiments of an exemplary V-VIS device that includes a contact lens 40 overlying a cornea 30 and iris 31. The contact lens 40 is corneal or scleral, or any combination thereof. One exemplary embodiment utilizes off-axis projection, as described in FIG. 2. For example, a projector 13 is mounted external to a contact lens 40, which contains light emitting particles. Excitation light 15 from the projector creates the moving aperture effect within or on the contact lens surface using any of the exemplary processes described herein, such as those described in FIG. 2.

In another embodiment, also shown in FIG. 4B, the contact lens 40 has one or more carrier layers 29, as described in FIGS. 3A and 3B, each of which include active optical material 24 defining one or more apertures 23. One or more antennas, such as antenna 27, receive signals that include instructions on the sequence, duration of, and interval between activation of the apertures. FIG. 4B shows a moving aperture at one position during a single sampling period of time.

In one example, the received signals may include radio frequency signals, and the antenna 27 may include a radio frequency antenna capable of receiving the radio frequency signals. The disclosed exemplary embodiments are not limited to radio frequency signals and antennas, and in other examples, the antenna 27 may be capable of receiving transmitted signals formatted in accordance with any additional, or alternate, communications protocols, such as those described herein.

Further, in some examples, the antenna 27 may receive the signals from a corresponding transmitter unit included within (or disposed on) eyeglasses worn by the subject, included within a mobile device operated by the subject or by a physician, or from any other appropriate device or system, e.g., across any of the communications networks described herein. The software instructions may, for instance, be generated or specified by the physician, and stored within one or more tangible, non-transitory memories of the eyeglasses, the mobile device, or the other appropriate device or system.

Figure 4C:
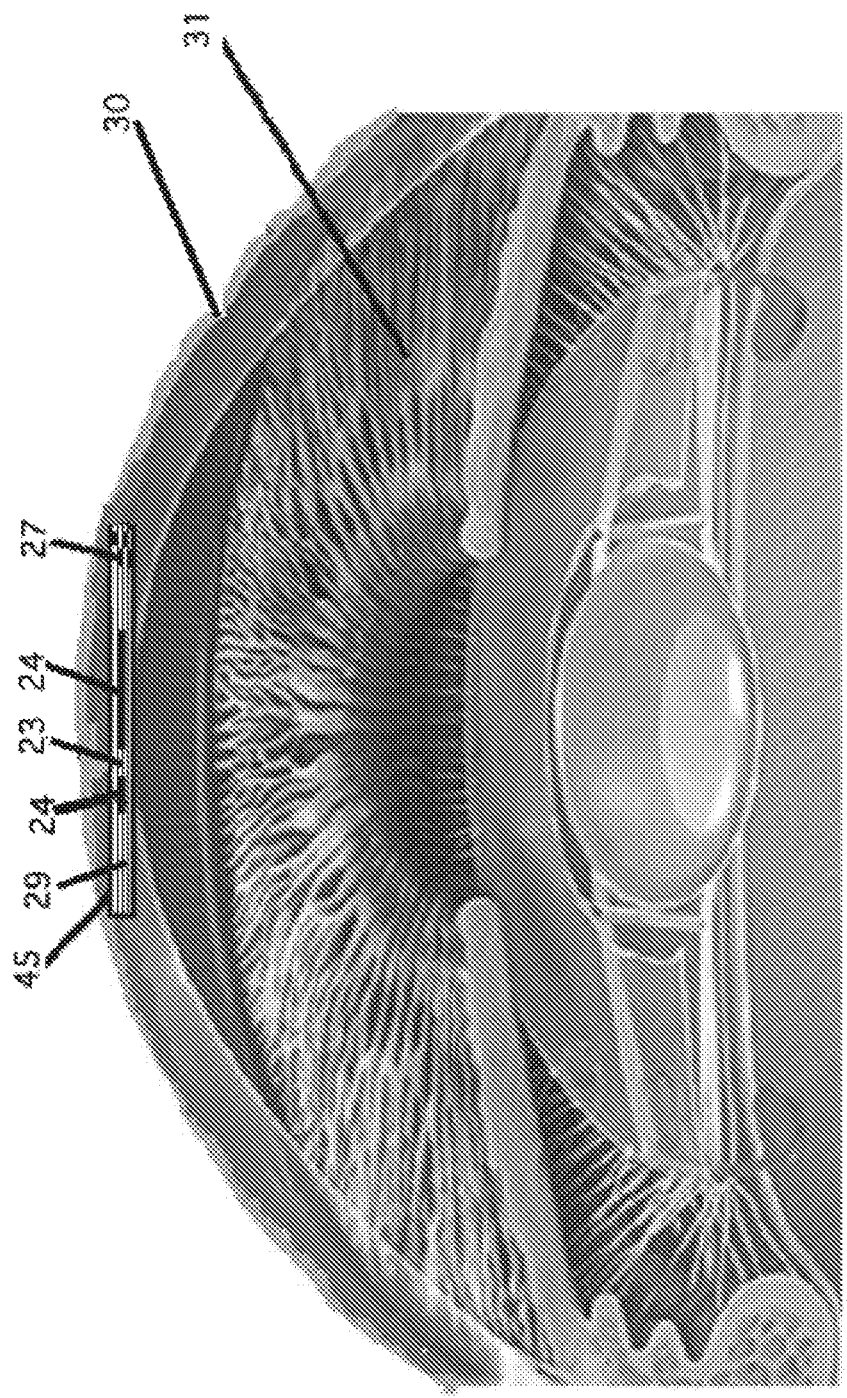
FIG. 4C is a side view of an eye with a light control device comprising a corneal inlay showing a moving aperture at one position during a single sampling time interval in accordance with some examples.

In FIG. 4C, the exemplary V-VIS device includes an intracorneal inlay 45, which includes one or more built-in antennas, such as the antenna 27, capable of receiving transmitted signals. Examples of the transmitted signals include, but not limited to, radio frequency signals or signals formatted in accordance with any additional, or alternate, communications protocols, such as those described herein.

The corneal inlay is placed within the cornea 30, which overlies the iris 31. When activated (e.g., based on signals received by the antenna 27), the active optical material 24 in the one or more transparent carrier layers 29 inside the corneal inlay 45 form one or more moving apertures 23. FIG. 4C shows a moving aperture at one position during a single sampling period of time.

Figure 4D:
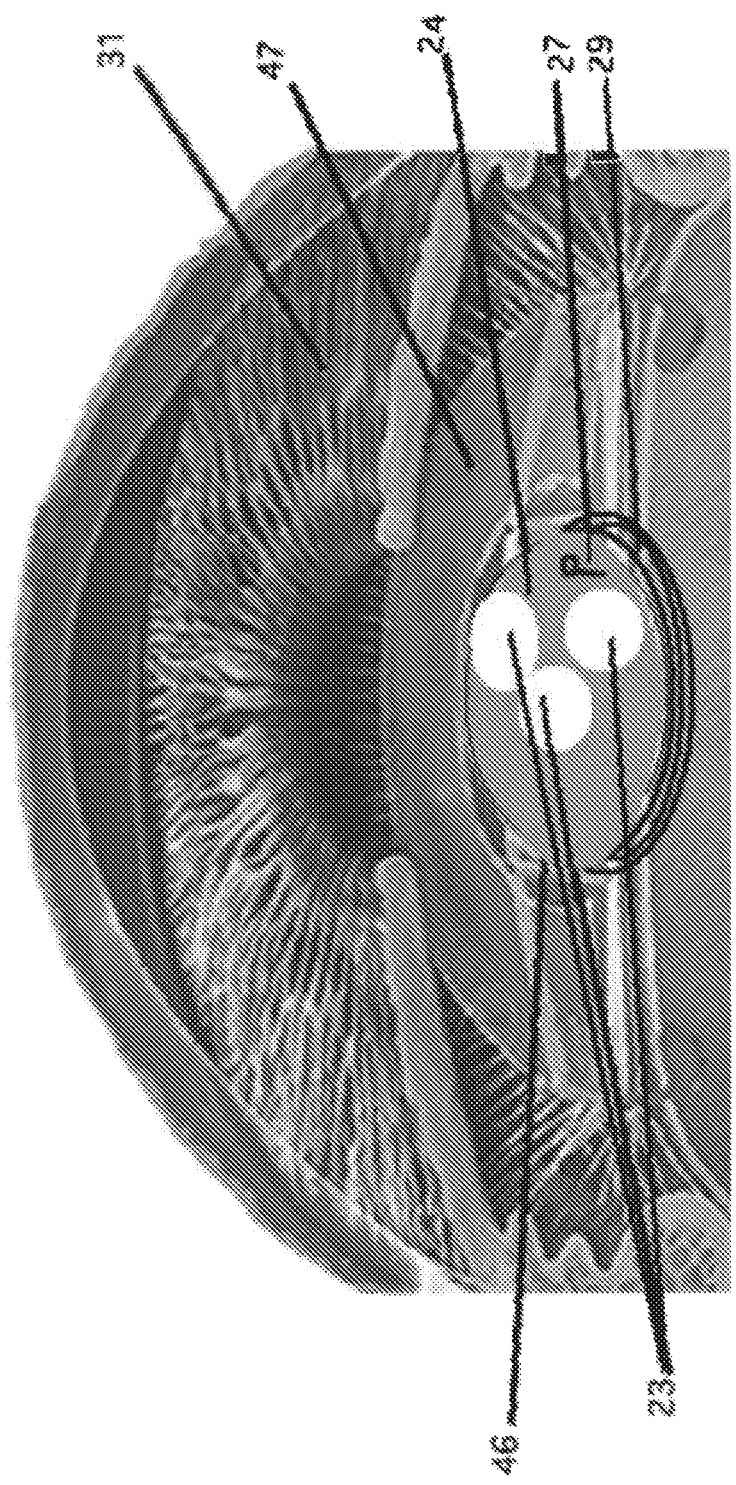
FIG. 4D is a side view of an eye with a light control device comprising an intraocular lens implant showing multiple moving apertures in one exemplary configuration during a single sampling time interval in accordance with some examples.

In FIG. 4D, the exemplary V-VIS device comprises an intraocular implant 46, which replaces a human crystalline lens and is usually placed inside the capsular bag 47 of the eye behind the iris 31, although it can be placed above the bag or above the iris 31 in some embodiments. The exemplary V-VIS device can include an intraocular device, an intraocular lens (IOL), an intraocular lens accessory device (IOLAD), or any combination thereof for insertion in a phakic, aphakic or pseudophakic eye, including at least one of an anterior chamber, sulcus-fixated, iris-fixated, capsular bag fixated or transcleral sutured IOL or IOLAD. When activated (e.g., based on signals received by one or more built-in antennas, such as the antenna 27), the active optical material 24 in the one or more transparent carrier layers 29 inside the implant form one or more moving apertures 23. FIG. 4D shows multiple moving apertures at one position during a single sampling period of time. The exemplary V-VIS device moves the one or more apertures by directing an electrical current (e.g., derived from signals received by the antenna 27) through each of one or more transparent carrier layers containing one or more active optical elements.

In some embodiments, a refractive error of an eye can be corrected by incorporating the appropriate lens for correction of ametropia into one or more of the exemplary V-VIS devices described herein, such as, but not limited to, spectacles, contact lens, corneal inlay, or intraocular lens.

In an exemplary embodiment, the power source for each carrier layer inside of a contact lens, corneal inlay or intraocular implant may be radio frequency (RF) transmission aided by rechargeable solar micro-batteries which may be built into corresponding ones of the exemplary V-VIS devices. For example, a micron size solar powered micro-battery, which provides added power to extend the range of radio frequency (RF) power sources to its RF antennas, can be incorporated into one or more of these exemplary V-VIS devices.

Figure 5:
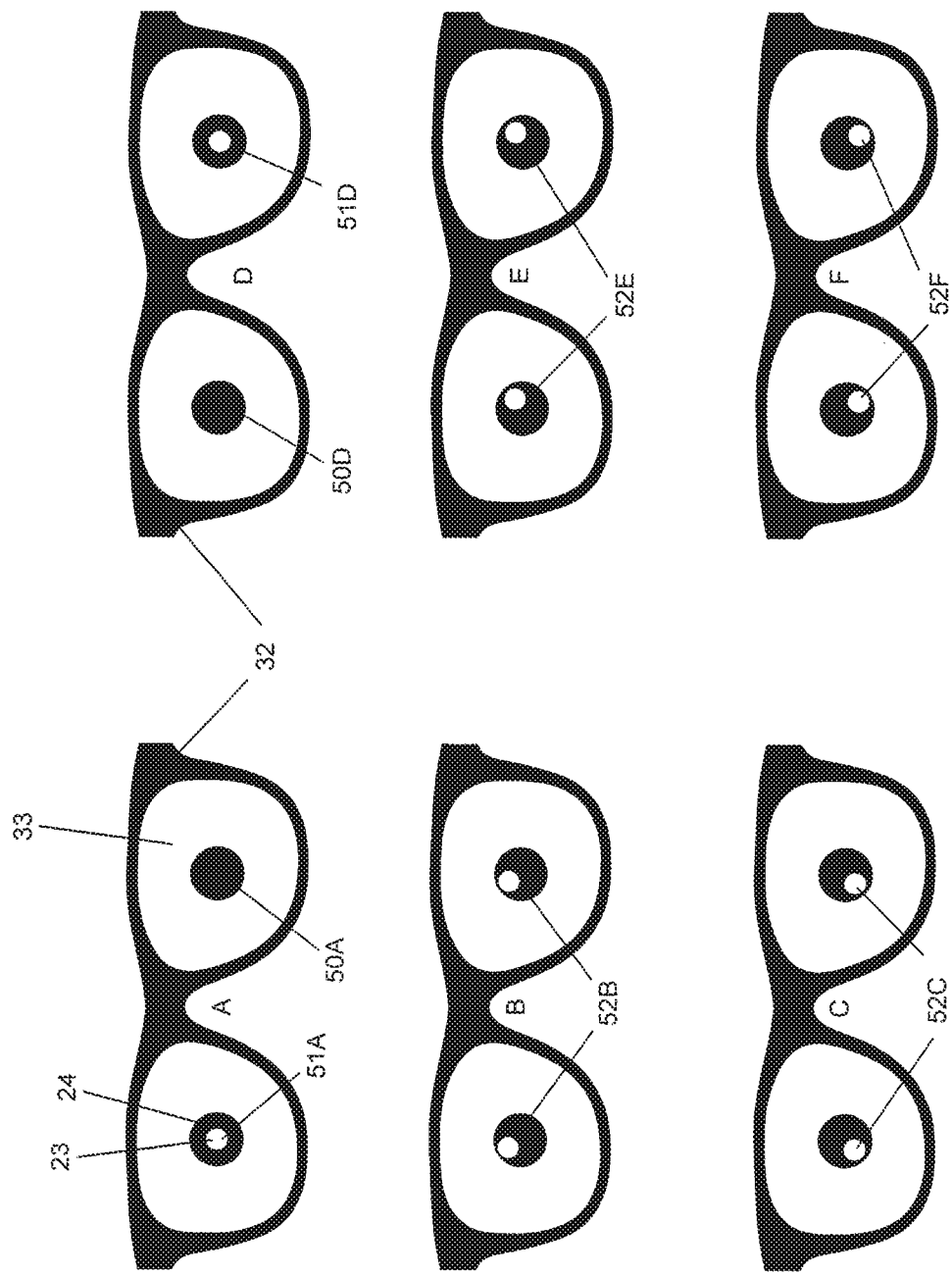
FIG. 5 depicts a light control device comprising a pair of spectacles viewed at different points in time, in accordance with some examples.

FIG. 5 shows six different moments in time (e.g., moments A-F), with five possible aperture positions. As illustrated in FIG. 5, a transparent aperture 51A in the position coaxial with the center of the pupil alternates during different sampling cycles with an opaque aperture 50D in the position coaxial with the center of the pupil in each lens. Further, in FIG. 5, an exemplary V-VIS device includes a pair of spectacles configured to treat a subject with amblyopia. The exemplary V-VIS device may be built into the lenses 33 of spectacle frames 32.

In some embodiments of an exemplary V-VIS device that treats amblyopia, the entire central view in front of an eye is obstructed (e.g., 50A and 50D) for a least one sampling cycle, while a central transparent aperture coaxial with the center of the pupil appears simultaneously in front of the fellow eye (e.g., 51A and 51D). The completely obstructed central view alternates between the two eyes after every sampling cycle or after every several sampling cycles. At the other sampling intervals (Sis) during each sampling cycle, transparent apertures appear in front of both eyes in positions that are non-coaxial with the center of the pupil, e.g., in 52B, 52C, 52E, and 52F. The apertures and surrounding opaque areas can be colored or opaque to desired densities from 10% to 100% opaque, depending on the density and type of optically active material placed in the one or more carrier layers of the exemplary V-VIS device. The aperture positions change at a pre-determined sampling rate (SR) between 50 hertz and 50 kilohertz. Depending upon the severity and type of amblyopia, the presentation duration, the color and/or the density of the central opacity, e.g., 50A and 50D can be adjusted to last longer or to be denser to strengthen and/or improve visual pathways and perception of the amblyopic eye or eyes.

Some embodiments of the exemplary V-VIS devices and methods, as described herein, overcome limitations of conventional therapies for amblyopia, including, but not limited to, inadequate improvement of visual function because of lack of intensive bilateral stimulation of visual pathways and/or obstruction of peripheral fields and/or compliance problems. The visual periphery has been documented to be relatively spared from vision loss in amblyopia. Conventional treatment for amblyopia, unlike some embodiments of these exemplary V-VIS devices and methods, decreases the number of spatial samples, particularly in the periphery, available for accurate integration of visual information and often results in loss of binocularity and/or inability to improve binocularity during treatment, as well as impairment of the ability to integrate peripheral visual field information in the visual cortex. Unlike conventional shutter or flicker glasses for amblyopia that block the peripheral view, some embodiments of the exemplary V-VIS devices for amblyopia preserve the visual representations of the peripheral visual field, because the peripheral view is never obstructed. Conventional visual training for amblyopia using conventional electronic devices with virtual reality (VR) displays cannot be used during normal activities, are used only for short training sessions and do not improve vision while the visually impaired subject is viewing objects in a natural scene or during normal visual tasks. Some embodiments of V-VIS therapy for amblyopia (e.g., which utilize one or more of the exemplary V-VIS devices and methods described herein), unlike conventional amblyopia treatments, allow for intensive binocular stimulation, which engages plasticity mechanisms in the entire visual pathway of FIG. 1. Some eyes with amblyopia also have dystrophic retinal cells. Unlike conventional glasses for amblyopia, some embodiments of the exemplary V-VIS devices for amblyopia can be configured to increase or decrease stimulation of different retinal areas because of the moving apertures, as well as the combination of AR or VR with one or more of the exemplary V-VIS methods and device in some configurations. Beneficial stimulation for amblyopia may be enhanced in some embodiments of the exemplary V-VIS methods and devices by adding red, green, or blue color to the central opaque region in order to isolate the excitation of individual sets of cone photoreceptors.

One or more of the extraocular V-VIS devices shown in the preceding figures, such as eyeglasses, an eyeglass accessory device, heads up display, visor, contact lens and a viewing screen, including, but not limited to, a remotely accessible-television, computer or mobile device, may be utilized for at least one of screening for V-VIS effects, customization of V-VIS, calibration of V-VIS, vision measurement, vision monitoring or any combination thereof. In one embodiment of the exemplary V-VIS methods and devices described herein, the SR would be set at rate too fast to allow perception and gradually slowed until the subject could first perceive a visual target. In some embodiments, this SR not only would allow for customization of the V-VIS treatment based on patient-provided feedback but also would define a functional measurement of the person's visual processing ability, which would vary between subjects, depending upon their age and underlying ophthalmic or neurologic disorders. Thus, the V-VIS devices and methods could be utilized diagnostically.

Figure 6:
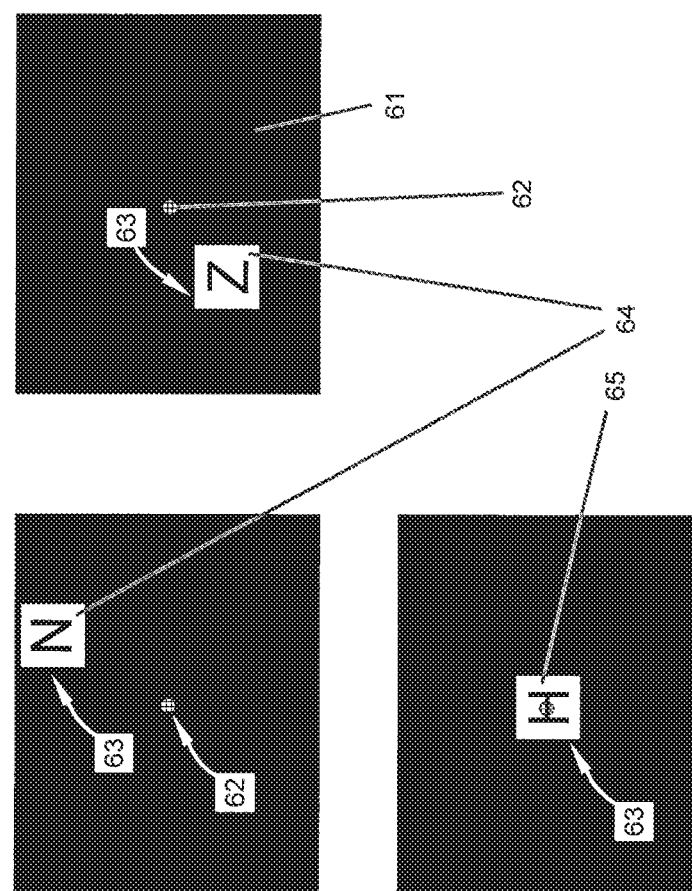
FIG. 6 depicts a light control device comprising a remotely accessible device, according to some examples.

Another embodiment of the exemplary V-VIS methods and devices is depicted in FIG. 6. In FIG. 6, the viewing screen of one or more of the exemplary V-VIS devices described herein (e.g., a remotely accessible-television, computer or mobile device, etc.) may present, to a subject, a display 61 that includes letters, numbers and/or objects of varying locations, sizes and/or contrast delivered to the retina by one or more moving revealing apertures. By way of example, display 61 may include a portion of an eye chart, which may be selectively and variably obscured by the moving apertures.

In some instances, the subject may establish a channel of communications with a testing, diagnostic, monitoring, or testing facility by telephone, (e.g., by dialing a toll-free number), by instant messaging, or through other internet-based or electronic communications mechanisms. Referring to FIG. 6, the subject may be directed to fixate on a target coaxial with the center of the pupil (e.g., target 62 of FIG. 6) on an otherwise darkened display 61 (e.g., by contrast). At least one revealing aperture 63 is moved at a rate between 50 hertz and 50 kilohertz between one or more positions 64 anterior to the retina on the display that are non-coaxial with the center of the pupil (e.g., revealing characters "Z" and "N" within the eye chart) and a position 65 anterior to the retina on the display 61 that is coaxial with the center of the pupil (e.g., revealing character "H" of the eye chart). As illustrated in FIG. 6, the at least one revealing aperture 63 (e.g., at positions 64 and 65) delivers to the retina a portion of the display 61's total field of view otherwise obscured by the darkened screen and the display 61's total field of view includes test images.

The subject's visual perception of the test images is measured and monitored by the subject's responses using recording and data collection methods known to those skilled in the art. For example, the subject may provide information identifying each of the letters or numbers visible within display 61 to the facility across the established channel of communications, and a computing system maintained by the facility may receive the provided information (e.g., through one or more programmatic interfaces or based on input provided by an agent or employee of the facility).

The computer may, in some instances, execute stored software instructions that generate (and store) a record of the identified letters and numbers, and that determine one or more letters or numbers missed by the subject based on a comparison between the identified record and information characterizing the movement and positioning of the at least one revealing aperture relative to the text images. Based on the determination, the computer may perform operations that generate a map of the of the subject's full visual field using any of the exemplary V-VIS methods described herein. For example, the generated map may identify a position or a size of a scotoma exhibited by the subject and additionally, or alternatively, an area of metamorphopsia exhibited by the subject. Further, variations of the size of the presented letters or numbers may facilitate a determination of a potential visual acuity of the subject based on the generated map. Some embodiments of the exemplary V-VIS devices and methods described herein measure and monitor visual perception and/or vision more conveniently and/or more accurately than conventional devices and methods.

In some embodiments, an exemplary V-VIS light control device may include one or more layers disposed anterior to a retina of an eye, or to retinas of both eyes, of a subject. The one or more layers may, for example, be placed extraocularly and may include one or more apertures. In further examples, described herein, one or more motors coupled to the one or more layers, when activated and powered by a corresponding source of electric energy, may control a movement of the one or more layers in front of one eye or both eyes, and the movement of the one or more layers may generate a moving aperture effect that samples and delivers to the retina environmental light from an ocular field of view at a sampling rate between 50 hertz and 50 kilohertz.

FIGS. 7A-7E illustrate components of an exemplary V-VIS device 70, in accordance with some exemplary embodiments. For example, as illustrated below in FIGS. 7A-7E, V-VIS device 70 may include an aperture-containing layer, such as layer 71, having one or more apertures 73, and layer 71 may be loosely suspended within a portion of a frame 75 (e.g., a spectacle or other appropriate frame) via one or more pairs of opposing magnets. Layer 71 may also be coupled mechanically (e.g., on a permanent or temporary basis) to a motor that, when activated, generates at least one of a translational, oscillatory, or rotational movement of layer 71 with respect to the frame 75. The at least one translational, oscillatory, or rotational movement of layer 71 may generate the exemplary moving aperture effect described herein, which samples and delivers to the retina the environmental light from the ocular field of view at the sampling rate between 50 hertz and 50 kilohertz.

Figure 7A:
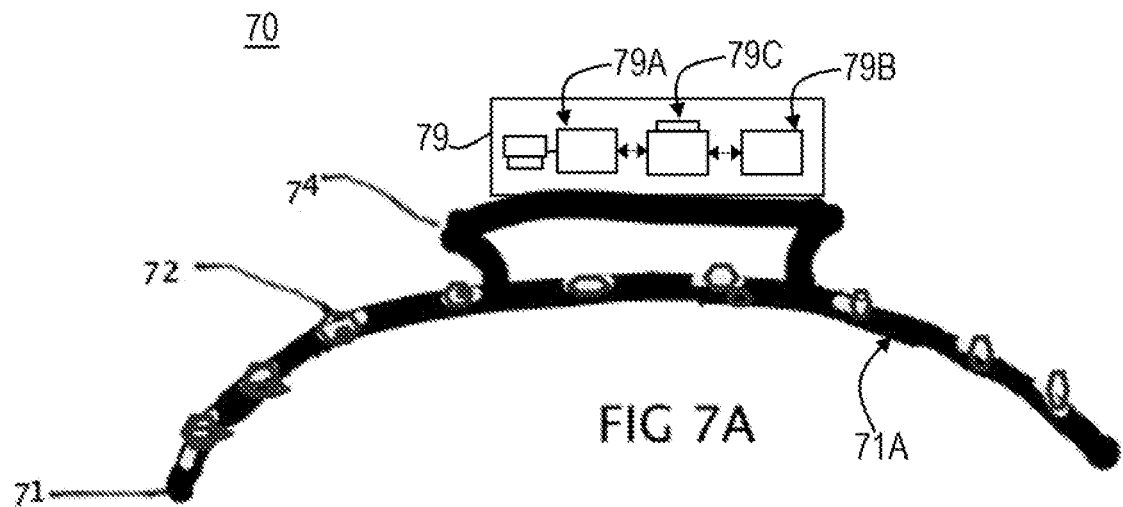
FIGS. 7A-7E, 8A-8D, and 9 illustrate exemplary light control devices, according to some examples.
Figure 7B:
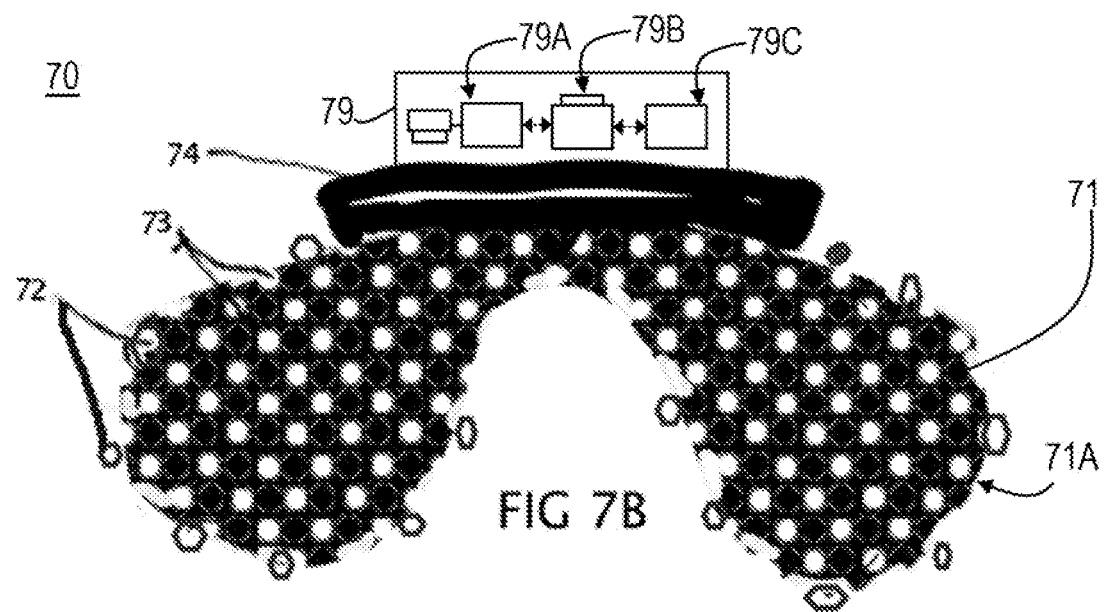
Figure 7C:
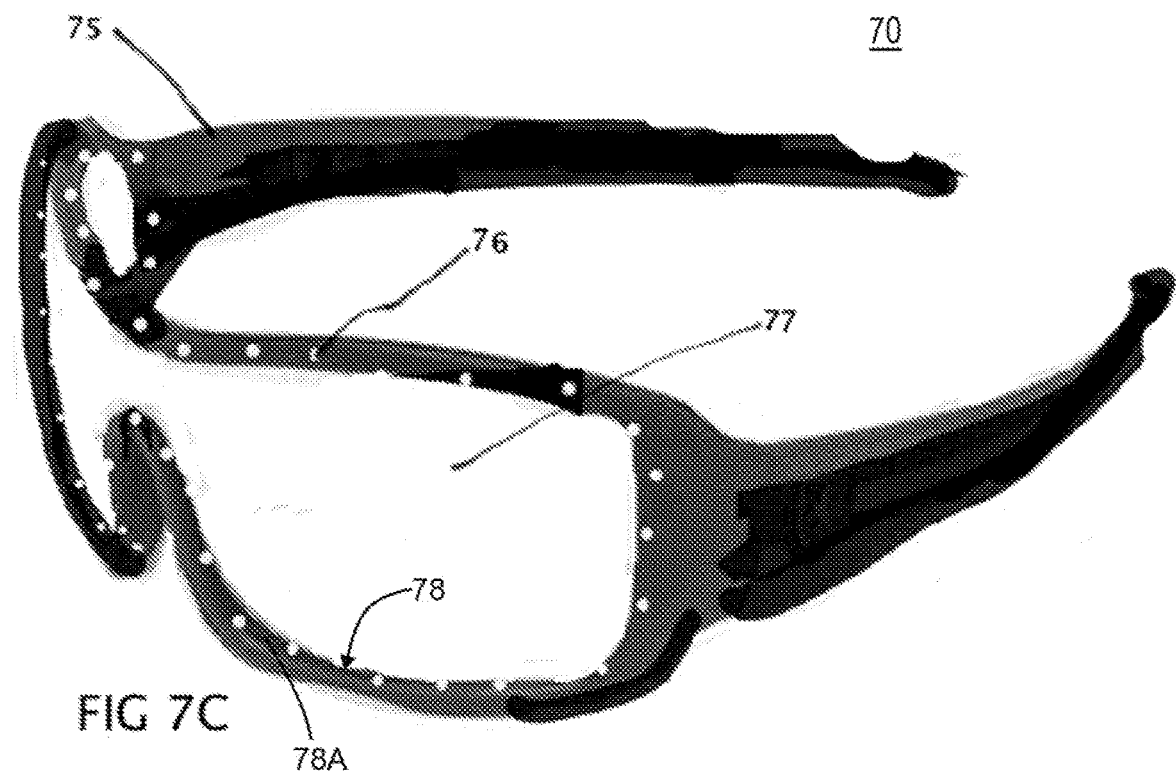
Figure 7D:
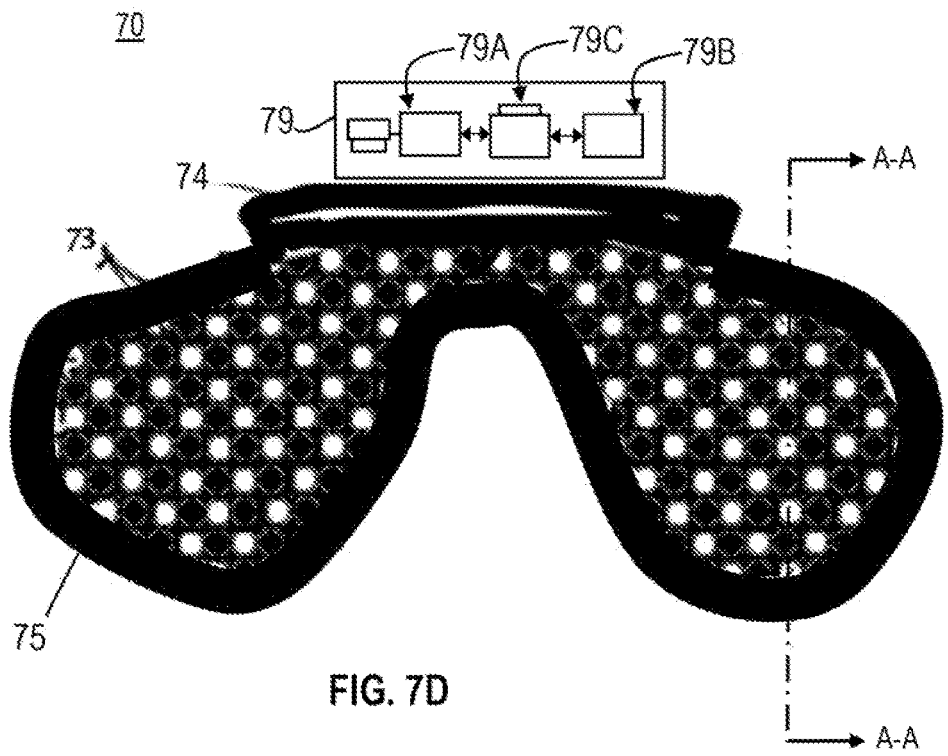
Figure 7E:
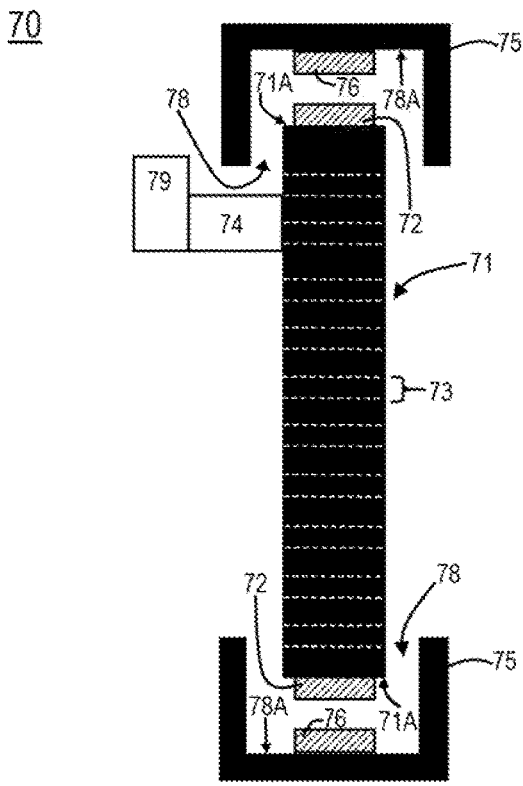

FIG. 7A illustrates an overhead view of layer 71 and its connection and control components, while FIG. 7B illustrates a front view of layer 71 and its connection and control components. FIG. 7C illustrates a perspective view of frame 75, which may include a frame opening 77 and a groove 78 along an interior surface of frame opening 77. FIG. 7D illustrates a front view of layer 71 and frame 75, when assembled into V-VIS device 70, and FIG. 7E is a diagram of a sectional view that illustrates the assembly of layer 71 and frame 75 into V-VIS device 70

Layer 71 may be characterized by a shape similar to that of frame opening 77 of frame 75, and as illustrated in FIGS. 7A and 7B, a plurality of first magnets 72 may be disposed along an edge surface 72A of layer 71. First magnets 72 may be disposed at regular intervals along edge surface 71A, and may be affixed to edge surface 71A using a mechanical adhesive, or may be integrated into layer 71. Further, layer 71 may also include a support structure 74 to which one or more control components 79 may be affixed on a permanent or temporary basis (e.g., via a mechanical adhesive, a clip, etc.). Control components 79 may, for example, include a motor 79A, a battery 79B, and an on-off switch 79C capable of delivery electrical energy from battery 79B to motor 79A, e.g., to activate motor 79A. Examples of motor 79A may include, but are not limited to, a rotary motor, a reciprocating motor, or a miniature vibrating motor (e.g., an eccentric rotating mass vibration motor or a linear resonant actuator), and motor 79A may be activated by battery 79B via on-off switch 79C.

Further, and referring to FIG. 7C, a plurality of second magnets 76 may be disposed along a groove surface 78A of groove 78 within frame 75, and each of second magnets 76 may be affixed to groove surface 78A using a mechanism adhesive, or may be integrated into frame 75. As illustrated in FIGS. 7D and 7E, and when assembled into V-VIS device 70, edge surface 71A of layer 71 may be disposed into, and may fit loosely within, groove 78 of frame 75 (e.g., frame 75 may be assembled from multiple components such that layer 71 is positioned within opening 77 of frame 75, and within grove 78). Further, first magnets 72 and second magnets 76 may be disposed at positions along respective ones of edge surface 71A and groove surface 78A such that each of first magnets 72 is held in opposition to a corresponding one of second magnets 76 having the same polarity positioned along groove surface 78A, as illustrated in FIG. 7E.

In some exemplary embodiments, and upon activation of on-off switch 79C by a wearer, battery 79B may supply electrically energy to motor 79A (e.g., which activates motor 79A), and now-activated motor 79A may generate a movement of layer 71 relative to frame 75 (and within frame opening 77) at a rate between 50 hertz and 50 kilohertz. Further, the magnetic forces generated by the opposing pairs of first and second magnets 72 and 76 may suspend now-moving layer 71 within frame opening 77, thus reducing (or eliminating) any potential impediment or dampening of the vibrational energy by frame 75, while reducing (or eliminating) a transmission of vibrational energy to the wearer.

FIGS. 8A-8D illustrate an additional V-VIS device 80, in accordance with some exemplary embodiments. For example, as illustrated below in FIGS. 8A-8D, V-VIS device 80 may include an aperture-containing layer, such as layer 81, having one or more apertures 83, and may also be coupled mechanically (e.g., on a permanent or temporary basis) to a motor that, when activated, generates at least one of a translational, oscillatory, or rotational movement of layer 81 with respect to the frame 85. As described below in reference to FIGS. 8A-8D, layer 81 may be connected to frame 85 by one or more springs 82 that, upon activation of the motor, may isolate frame 85 from the vibrational movement of layer 81 and reduce any dampening of the vibrational movement of layer 81.

Figure 8A:
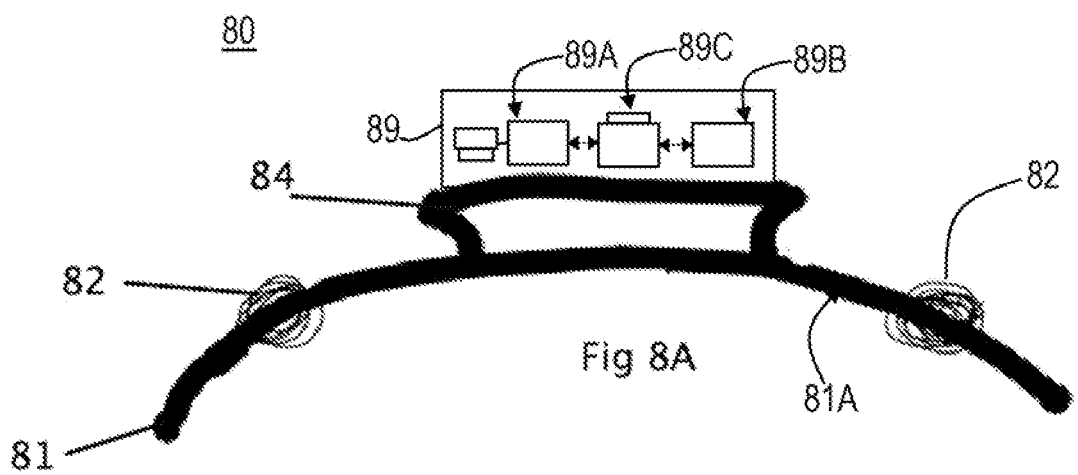
Figure 8B:
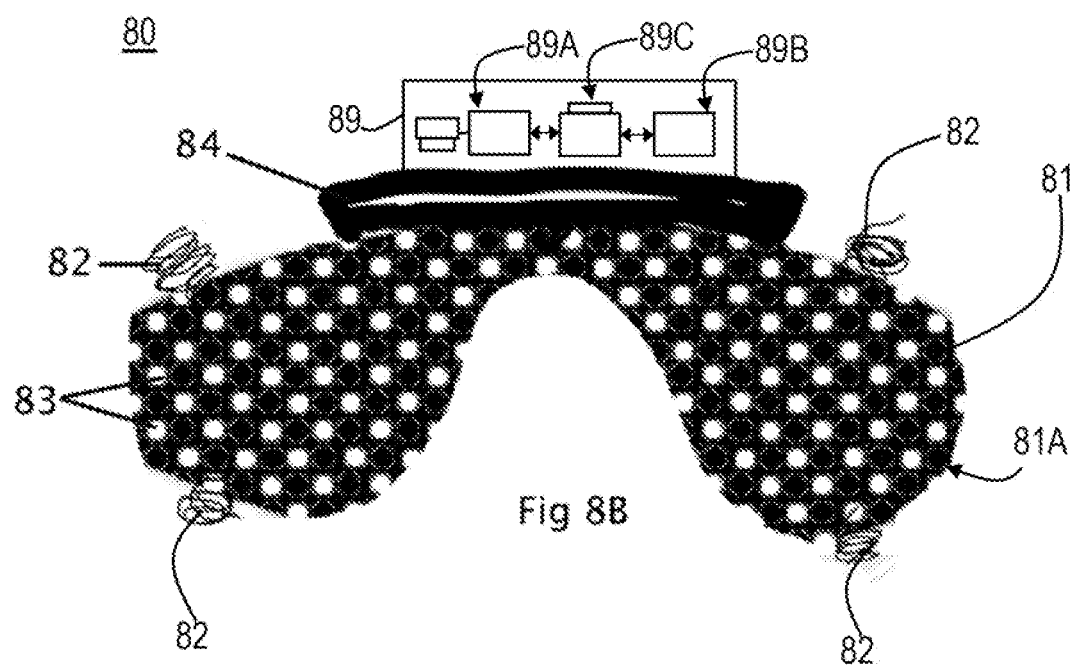
Figure 8C:
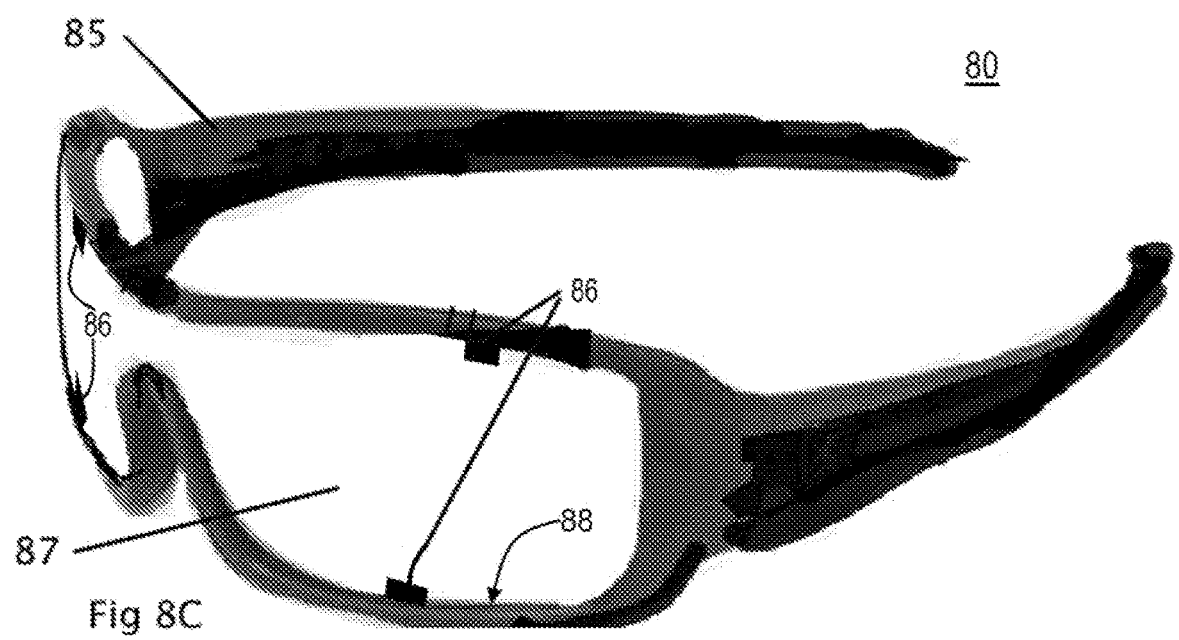
Figure 8D:
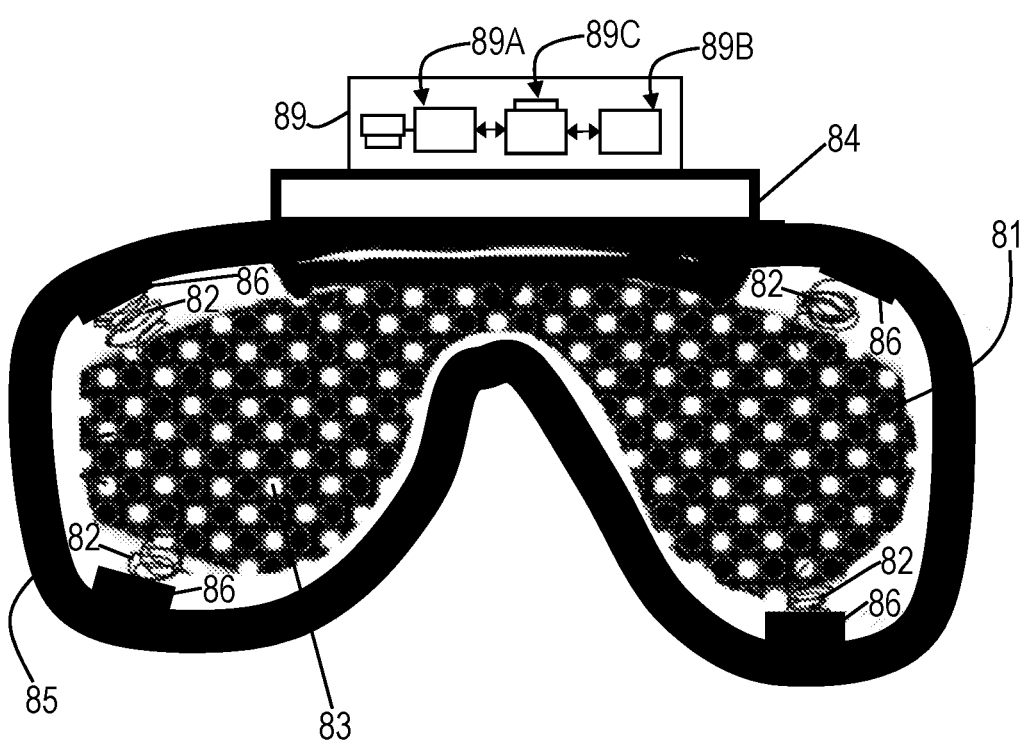

FIG. 8A illustrates an overhead view of layer 81 and its connection and control components, while FIG. 8B illustrates a front view of layer 81 and its connection and control components. FIG. 8C illustrates a perspective view of frame 85, which may include a frame opening 87, and FIG. 8D illustrates a front view of layer 81 and frame 85, when assembled into V-VIS device 80. In some instances, layer 81 may be characterized by a shape similar to that of frame opening 87 of frame 85, and as illustrated in FIGS. 8A and 8B, the one or more of springs 82 may be disposed along an edge surface 81A of layer 81.

Further, layer 81 may also include a support structure 84 to which one or more control components 89 may be affixed on a permanent or temporary basis (e.g., via a mechanical adhesive, a clip, etc.). Control components 89 may, for example, include a motor 89A, a battery 89B, and an on-off switch 89C capable of delivery electrical energy from battery 89B to motor 89A, e.g., to activate motor 89A. Examples of motor 89A may include, but are not limited to, a rotary motor, a reciprocating motor, or a miniature vibrating motor (e.g., an eccentric rotating mass vibration motor or a linear resonant actuator), and motor 89A may be activated by battery 89B via on-off switch 89C.

Further, and referring to FIG. 8C, one or more spring mounts 86 may be disposed along an interior surface 88 of frame opening 87, and may be to receive, and establish a connection with, corresponding ones of springs 82. As illustrated in FIG. 8D, and when assembled into V-VIS device 80, each of springs 82 may be connected to a corresponding one of spring mounts 86 (e.g., frame 85 may be assembled from multiple components such that layer 81 is position within opening 87 of frame 85). In some exemplary embodiments, and upon activation of on-off switch 89C by a wearer, now-energized motor 89A may generate a movement of layer 81 relative to frame 85 (and within frame opening 87) at a rate between 50 hertz and 50 kilohertz. Further, each of connected springs 82 and spring mounts 86 may suspend now-moving layer 81 within frame opening 87, thus reducing (or eliminating) any potential impediment or dampening of the vibrational energy by the frame, while reducing (or eliminating) a transmission of vibrational energy to the wearer.

In other exemplary embodiments, one or more of the V-VIS light control devices described herein may include two or more layers with apertures in front of an eye or both eyes, which may be placed one atop the other, with at least one layer moved at rate between 50 hertz to 50 kilohertz to produce the moving aperture effect.

Figure 9:
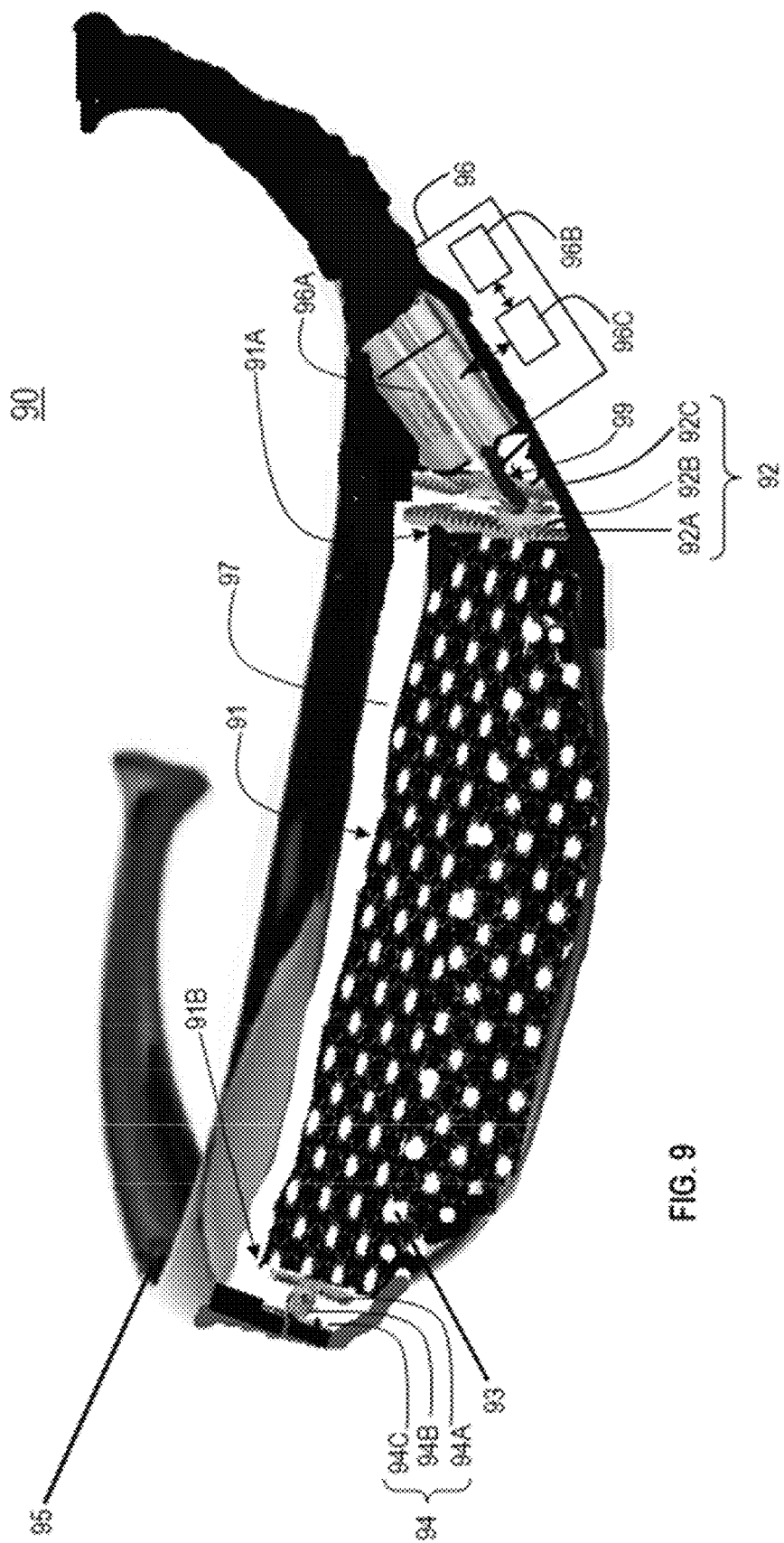

FIG. 9 illustrates a further V-VIS light control device 90, in accordance with some exemplary embodiments. For example, as illustrated in FIG. 9, V-VIS light control device 90 may include a frame 95 having a corresponding frame opening 97, into which an aperture-containing layer, e.g., layer 91, having one or more apertures 93 may be disposed. As further illustrated in FIG. 9, an end portion 91A of layer 91 may be coupled to a first rack-and-pinion mechanism 92, and an end portion 91B of layer 91 may be coupled to a second rack-and-pinion mechanism 94. For example, end portion 91A may be connected to a proximate rack 92A of first rack-and-pinion mechanism 92, and a rack-and-pinion gear 92B may operatively couple proximate rack 92A to a distal rack 92C of first rack-and-pinion mechanism 92, which may be connected to frame 95 at corresponding attachment points (not illustrated in FIG. 9). Similarly, and by way of example, end portion 91B may be connected to a proximate rack 94A of second rack-and-pinion mechanism 94, and a rack-and-pinion gear 94B may operatively couple proximate rack 94A to a distal rack 94C of second rack-and-pinion mechanism 94, which may be connected to frame 95 at corresponding additional attachment points (not illustrated in FIG. 9).

V-VIS device 90 may also include control components 96, which may be attached to frame 95 (e.g., either permanently, or on a temporary basis). Control components 96 may, for example, include a motor 96A, a battery 96B, and an on-off switch 96C capable of delivery electrical energy from battery 96B to motor 96A, e.g., to activate motor 96A. In some instances, a shaft 99 of motor 96A may be coupled to rack-and-pinion gear 92B of first rack-and-pinion mechanism 92, and upon activation of motor 96A by the wearer, e.g., using on-off switch 98C, shaft 99 may drive rack-and-pinion gear 92B, which generates an up-and-down movement of layer 91 along proximate and distal tracks 92A and 92B (and further, along proximate and distal tracks 94A and 94B) at a rate between 50 hertz and 50 kilohertz, e.g., depending on the speed of motor 96A.

By way of example, each of first rack-and-pinion mechanism 92 and second rack-and-pinion mechanism 94 may include a reciprocal rack-and-pinion mechanism, and motor 98A may include a rotary motor capable of driving a corresponding rack-and-pinion gear, such as rack-and-pinion gear 92B. In other instances, not illustrated in FIG. 9, motor 98A may include a reciprocating motor, and each of first rack-and-pinion mechanism 92 and second rack-and-pinion mechanism 94 may include a non-reciprocal rack-and-pinion mechanism.

Further, and in some examples, one or more of layer 71, layer 81, or layer 91 may be formed from an opaque material, such as a plastic material, and the one or more apertures 73, 83, and 93 may be formed within corresponding ones of layers 71, 81, and 91 using any technique appropriate to the opaque materials, such as drilling, milling, punching, or molding. In other examples, and as described herein, one or more of layer 71, layer 81, or layer 91 may include one or more of the transparent layers described herein, which may be disposed anterior to the retina of the eye or to the retinas of both eyes.

For instance, layer 91 of V-VIS light control device 90 may include a transparent layer having apertures 93, which may be generated using optically activated elements based on any of the exemplary processes described herein. Additionally, or alternatively, the transparent layer that forms layer 91 may also include one or more physical apertures generated using any appropriate technique. As described herein, exemplary V-VIS light control device 90 may produce the moving aperture effect mechanically using a motor connected to layer 91 (e.g., by reciprocal rack-and-pinion gearing) to provide a reciprocating movement at a rate between 50 hertz and 50 kilohertz. In such a configuration, the one or more moving apertures may be coaxial or non-coaxial with a pupil of one or both eyes.

One or more of the exemplary V-VIS devices and methods, as described herein, include or utilize a light control device to move one or more apertures anterior to a retina between one or more positions anterior to the retina that are non-coaxial with a center of a pupil and a position anterior to the retina that is coaxial with the center of the pupil. The one or more apertures may, for example, be moved at a rate between 50 hertz and 50 kilohertz, thereby to produce a regional variation of visual information and sampling (V-VIS) of the ocular field of view. Further, the phrase "anterior to the retina" includes one of extraocular, intracorneal or intraocular placement, and the device can electrooptically move the one or more apertures through one or more see-through displays placed anterior to the retina.

In further embodiments, the light control device can be utilized for at least one of V-VIS by a subject, for at least one of screening for use of V-VIS, customization of V-VIS, calibration of V-VIS, V-VIS vision measurement, V-VIS vision monitoring, or any combination thereof. In some instances, the V-VIS device can be configured to produce at least one of an improvement of vision in an eye or both eyes of a subject, a stabilization of vision in an eye or both eyes of a subject, a correction of an ophthalmic or neurologic condition, an amelioration of a visual symptom in an eye or both eyes of a subject with an ophthalmic or neurologic condition, disease, injury or disorder, a reduction of a rate of vision loss compared to an untreated control group in an eye or both eyes of a subject with vision loss from an ophthalmic or neurologic condition, disease, injury or disorder, a reduction of a rate of progression of an ophthalmic condition, disease or disorder compared to an untreated control group in an eye or both eyes of a subject with an ophthalmic condition, disease, or disorder, a vision measurement of an eye or both eyes of a subject, a vision monitoring of an eye or both eyes of a subject, or any combination thereof.

In some embodiments, one or more of the exemplary V-VIS devices and methods combine V-VIS teachings with certain ophthalmic and neurologic treatments. Some therapeutic embodiments include treating an eye with a method comprising utilization of a V-VIS device, together with administration of another therapy for an ophthalmic or a neurologic condition, disease, injury or disorder.

The V-VIS device can be configured to move optically one or more apertures anterior to a retina of an eye between one or more positions anterior to the retina that are non-coaxial with a center of a pupil and an position anterior to the retina that is coaxial with the center of the pupil (e.g., in accordance with any of the processes described herein), and the one or more apertures are moved at a rate between 50 hertz and 50 kilohertz, In some embodiments, one or more of the exemplary V-VIS devices and methods can be combined with other ophthalmic and neurologic treatments that include, but are not limited to: pharmacological and/or nutritional supplemental and/or laser and/or radiation and/or retinal replacement and/or stem cell transplantation and/or epigenetic and/or genetic and/or optogenetic and/or retinal prosthetic and/or other therapy (hereafter other therapies) in order to improve treatment of ophthalmic conditions, diseases, injuries and disorders, including, but not limited to, macular degeneration and/or diabetic retinopathy and/or glaucoma and/or axial myopia and/or other neovascular and/or atrophic and/or inflammatory and/or inherited and/or nutritional and/or age-related retinal conditions, diseases, injuries or disorders (hereinafter "ophthalmic diseases") and/or neurologic diseases, disorders or conditions (hereinafter "neurologic diseases). Certain of the exemplary V-VIS devices and methods described herein overcome drawbacks and deficiencies of conventional therapies by introducing different mechanisms of visual sampling and/or visual processing and/or visual perception and/or retinal repair processes and/or neural repair processes associated with ophthalmic and/or neurologic diseases. Further, certain of the exemplary V-VIS devices and methods overcome drawbacks and deficiencies of other therapies by synergistically combining them with V-VIS to improve visual and/or anatomic outcomes, which also improves patient compliance with other therapy. In combination therapy with V-VIS, other therapy can be administered before, during or after V-VIS. In some embodiments of combination therapy, V-VIS treatment is administered either before non-V-VIS therapy or at some time following initiation of non-V-VIS therapy.

In some embodiments, V-VIS treatment can be combined with other therapies for ophthalmic and neurologic diseases, including but not limited to laser therapies, including but not limited to photobiomodulation, laser photocoagulation, laser photodynamic therapy, subthreshold micropulse laser therapy, glaucoma laser therapy, (including, but not limited to, laser trabeculoplasty and cyclophotocoagulation), glaucoma filtration surgery (including, but not limited to, trabeculectomy, microtrabeculectomy, internal or external tube shunt implantation, suprachoroidal shunt implantation), vision correction (including, but not limited to, refractive surgery, laser vision correction and genetic therapy), optic nerve surgery (including, but not limited to, decompression and repair surgery), retinal prostheses, stem cell transplantation, and radiation therapy (including but not limited to focal intraocular strontium 90 beta radiation).

Some embodiments include treating an eye with V-VIS (e.g., based on a utilization of one or more of the exemplary V-VIS devices and methods described herein) in combination with administering at a time prior to V-VIS, during V-VIS, after V-VIS, or any combination thereof, at least one of a genetic, epigenetic, optogenetic, retinal replacement or stem cell therapy for treating an ophthalmic disorder. In further embodiments, a therapeutic or treatment method (e.g., a "combination" method) for treating an eye can include a utilization of a V-VIS device, together with administration, at a time prior to V-VIS, during V-VIS, after V-VIS or any combination thereof, of at least one of a genetic, epigenetic, optogenetic, retinal replacement or stem cell therapy for treating an ophthalmic or neurologic disease. As described herein, the device can be configured to move optically one or more apertures anterior to a retina of an eye between one or more positions anterior to the retina that are non-coaxial with a center of a pupil and an area anterior to the retina that is coaxial with the center of the pupil (e.g., in accordance with any of the processes described herein), and the one or more apertures are moved at a rate between 50 hertz and 50 kilohertz.

In some embodiments of combination therapy, V-VIS treatment improves and/or facilitates and/or expedites recovery and/or restoration of visual functioning, including, but not limited to, at least one of neural connectivity, neural integration, visual sampling or visual perception after genetic, epigenetic, optogenetic, retinal replacement or stem cell therapy. In some embodiments, the combination of V-VIS with retinal replacement and/or stem cell therapy, overcomes limitations of retinal replacement and/or stem cell therapy, including, but not limited to incorrect or inadequate targeted delivery of stem cells or other retinal cells. In some embodiments, treatment for retinal dystrophies and/or degenerations combined with V-VIS treatment, unlike retinal prostheses and optogenetic therapy alone, overcomes limitations in dystrophic retinas, including, but not limited to, aberrant remodeling of intraretinal connections and pathological spontaneous hyperactivity in dystrophic retinas. In some embodiments, treatment for retinal dystrophies and/or degenerations combined with V-VIS treatment overcomes limitations of retinal prostheses and optogenetic therapy in dystrophic retinas, including, but not limited to, central scotoma creation, because of displacement of retinal ganglion cells from the fovea, and color encoding difficulties, because of insufficient knowledge of which ganglion cells encode which color channels.

In further embodiments, one or more of the exemplary V-VIS devices and methods, as described herein, can be combined with anti-angiogenesis therapy for treating or ameliorating a symptom of a neovascular ophthalmic condition, disease, injury or disorder, including, but not limited to, a macular degeneration, a choroidal neovascularization and a diabetic retinopathy. Some embodiments include treating an eye with V-VIS (e.g., utilizing one or more of the exemplary V-VIS devices and methods described herein) in combination with administering, at a time prior to V-VIS, during V-VIS, after V-VIS or any combination thereof, a therapeutically effective amount of an anti-angiogenesis agent that is administered via intravitreal injections, orally, topically, intraretinally, via implants or via iontophoresis. As used herein, the term "ameliorating" or "treating" or "compensating for" means that the clinical signs and/or symptoms associated with an ocular disorder (e.g., macular degeneration) are lessened as result of the actions performed. The signs or symptoms to be monitored will be characteristic of the ocular disorder and will be well known to physicians skilled in the art, as well the methods for monitoring the signs, symptoms and conditions.

Combination therapy utilizing V-VIS together with anti-angiogenesis therapy would be advantageous over anti-angiogenesis alone or V-VIS alone, because the combination therapy would further improve functional vision, further stabilize functional vision, decrease treatment burden and/or improve patient compliance.

Some embodiments described herein provide a method of ameliorating or treating a neovascular ophthalmic condition, disease, injury or disorder by treating an eye with V-VIS (e.g., utilizing one or more of the exemplary V-VIS devices and methods) in combination with administering a therapeutically effective amount of an anti-angiogenesis agent, including but not limited to a vascular endothelial growth factor (VEGF) antagonist (an inhibitor of VEGF activity), including, but not limited to, aflibercept, ranibizumab, bevacizumab and brolucizumab.

Some embodiments described herein provide a method of ameliorating or treating a neovascular ophthalmic condition, disease, injury or disorder by treating an eye with V-VIS (e.g., utilizing one or more of the exemplary V-VIS devices and methods) in combination with administering a therapeutically effective amount of an anti-angiogenesis agent, including, but not limited to, a platelet-derived growth factor (PDGF) antagonist, including, but not limited to, volociximab and P200.

Some embodiments also provide a method of treating or ameliorating a neovascular ophthalmic condition, disease, injury or disorder by treating an eye with V-VIS (e.g., utilizing one or more of the exemplary V-VIS devices and methods) in combination with administering a therapeutically effective amount of an anti-angiogenesis agent, including, but not limited to, an angiopoietin antagonist including, but not limited to, or an angiopoietin-2 antagonist, including but not limited to, RG7716.

Some embodiments described herein provide a method of ameliorating or treating a neovascular ophthalmic condition, disease, injury or disorder by treating an eye with V-VIS (e.g., utilizing one or more of the exemplary V-VIS devices and methods) in combination with administering a therapeutically effective amount of an anti-angiogenesis agent, including, but not limited to, an endoglin antagonist, including, but not limited to, carotuximab.

Some embodiments described herein provide a method of ameliorating or treating a neovascular ophthalmic condition, disease, injury or disorder by treating an eye with V-VIS (e.g., utilizing one or more of the exemplary V-VIS devices and methods) in combination with administering a therapeutically effective amount of an anti-angiogenesis agent, including, but not limited to, an inhibitor of phosphorylation of VEGF and PDGF receptors, including but not limited to a tyrosine kinase inhibitor, including, but not limited to, vetalanib or pazopanibor.

Some embodiments described herein provide a method of ameliorating or treating a neovascular ophthalmic condition, disease, injury or disorder by treating an eye with V-VIS (e.g., utilizing one or more of the exemplary V-VIS devices and methods) in combination with administering a therapeutically effective amount of an anti-angiogenesis agent, including, but not limited to, an integrin antagonist, including, but not limited to, an anti-integrin peptide, an inhibitor of alpha5beta1 integrin activity and an oligopeptide binding to integrin receptor sites, including, but not limited to, luminate.

Some embodiments described herein provide a method of ameliorating or treating a neovascular ophthalmic condition, disease, injury or disorder by treating an eye with V-VIS (e.g., utilizing one or more of the exemplary V-VIS devices and methods) in combination with administering, at a time prior to V-VIS, during V-VIS, after V-VIS or any combination thereof, a therapeutically effective amount of two or more anti-angiogenesis agents, including but not limited to, any VEGF antagonist, any PDGF antagonist, any angiopoietin antagonist, any endoglin antagonist, and any integrin antagonist, wherein the two or more anti-angiogenesis agents are delivered together or sequentially.

In other embodiments, a method of treating or ameliorating an ophthalmic disease, such as, but not limited to, a neovascular ophthalmic disease and/or wet macular degeneration, and/or diabetic retinopathy, in a subject includes treatment with V-VIS (e.g., utilizing one or more of the exemplary V-VIS devices and methods) in combination with administering a therapeutically effective amount of an anti-inflammatory agent, including, but not limited to, fluocinolone acetonide, wherein the anti-inflammatory agent is administered via intravitreal injections, orally, topically, intraretinally, via implants or via iontophoresis.

In some embodiments, a method of treating or ameliorating an ophthalmic disease, such as, but not limited to, geographic atrophy and/or dry macular degeneration, in a subject includes treatment with V-VIS (e.g., utilizing one or more of the exemplary V-VIS devices and methods) in combination with administering via intravitreal injections, orally, topically, intraretinally, via implants or via iontophoresis. a therapeutically effective amount of an inhibitor of complement, including, but not limited to, an inhibitor of complement 3 or 5 activity, including, but not limited to, avacincaptad pegol, LEG 316, POT-,4, eculizumab, JPE- 1375, ARC1905, or a therapeutically effective amount of an anti-inflammatory agent, including, but not limited to, an antibiotic in the tetracycline class, including, but not limited to, doxycycline, or a therapeutically effective amount an immunomodulating agent, including, but not limited to, a T helper 2 inducer, including, but not limited to, glatiramer acetate.

In some embodiments, a method of treating or ameliorating an ophthalmic disease, such as, but not limited to, geographic atrophy and/or dry macular degeneration in a subject, includes treatment with V-VIS (e.g., utilizing one or more of the exemplary V-VIS devices and methods) in combination with administering a therapeutically effective amount of OT551, or any other down regulator of overexpression of the protein complex nuclear factor (NF)-,B or any other antioxidant, or combination of antioxidants, including but not limited to combinations of vitamin C, vitamin E, beta-carotene or lutein and zeaxanthin, and omega-3 fatty acids as in for, example, the Age-Related Eye Disease Study (AREDS) and AREDS 2 studies.

In some embodiments, a method of treating or ameliorating an ophthalmic disease, such as, but not limited to, geographic atrophy and/or dry macular degeneration in a subject, includes treatment with V-VIS (e.g., utilizing one or more of the exemplary V-VIS devices and methods) in combination with administering a therapeutically effective amount nicotinamide adenine dinucleotide (NAD) or any precursors of NAD, including but not limited nicotinamide riboside or nicotinamide mononucleotide.

In some embodiments, a method of treating or ameliorating an ophthalmic disease, such as, but not limited to, geographic atrophy and/or dry macular degeneration in a subject, including treatment with V-VIS (e.g., utilizing one or more of the exemplary V-VIS devices and methods) in combination with administering a therapeutically effective amount of a trophic factor including, but not limited to, pigment epithelium-derived factor (PEDF), fibroblast growth factors (FGFs) and lens epithelium-derived growth factor (LEDGF).

Some embodiments include treating an eye with V-VIS (e.g., utilizing one or more of the exemplary V-VIS devices and methods) in combination with administering topically, intraretinally, via intravitreal injections, via implants or via iontophoresis, at a time prior to V-VIS, during V-VIS, after V-VIS, or any combination thereof, a therapeutically effective amount of at least one of the following for treating an ophthalmic or neurologic condition, disease, injury or disorder, including, but not limited to, a glaucoma, a macular degeneration, an optic nerve atrophy, an autoimmune neurodegenerative disorder or a cerebrovascular accident: i. an intraocular pressure-lowering agent, including but not limited to a miotic, an alpha or alpha/beta adrenergic agonist, a beta-blocker, a Ca2+ channel blocker, a carbonic anhydrase inhibitor, a cholinesterase inhibitor, a prostaglandin agonist, a prostaglandin, a prostamide, a cannabinoid, or any combination thereof; ii. a retinal cell- or cortical cell-neuroprotective or neuroregenerative agent, including but not limited to a rho-kinase inhibitor, an adenosine receptor agonist, a glutamate antagonist, a neurotrophic factor or a neurotrophic factor regulator; or iii. any combination thereof. Such combination therapy would further improve functional vision, further stabilize functional vision, decrease treatment burden and/or improve patient compliance.

In some embodiments, a method of treating or ameliorating an ophthalmic or neurologic disease, such as, but not limited to, geographic atrophy and/or dry macular degeneration and/or glaucoma in a subject, includes treatment with V-VIS (e.g., utilizing one or more of the exemplary V-VIS devices and methods) in combination with administering a therapeutically effective amount of ciliary neurotrophic factor (CNTF) or any other neurotrophic factors or any other inhibitors of photoreceptor apoptosis.

In some embodiments, a method of treating or ameliorating an ophthalmic or neurologic disease, such as, but not limited to, geographic atrophy and/or dry macular degeneration and/or glaucoma in a subject comprising treatment with V-VIS (e.g., utilizing one or more of the exemplary V-VIS devices and methods) in combination with administering a therapeutically effective amount of a neuroprotective agent, including, but not limited, to brimodinine.

In some embodiments, a method of treating or ameliorating an ophthalmic or neurologic disease, such as, but not limited to, geographic atrophy and/or dry macular degeneration in a subject comprising treatment with V-VIS (e.g., utilizing one or more of the exemplary V-VIS devices and methods) in combination with administering a therapeutically effective amount of a Fas inhibitor or other agent designed to protect retinal cells from cell death.

In some embodiments, a method of treating or ameliorating an ophthalmic or neurologic disease, such as, but not limited to, geographic atrophy and/or dry macular degeneration and/or neovascular macular degeneration and/or glaucoma in a subject, includes treatment with V-VIS (e.g., utilizing one or more of the exemplary V-VIS devices and methods) in combination with administering a therapeutically effective amount of a statin, including, but not limited to, atorvastin, lovastation, rosuvastatin, fluvastatin or simvastatin.

In some embodiments, a method of treating or ameliorating an ophthalmic disease, such as, but not limited to, glaucoma or ocular hypertension, in a subject, includes treatment with V-VIS (e.g., utilizing one or more of the exemplary V-VIS devices and methods) in combination with administering a therapeutically effective amount of an intraocular pressure (TOP)—lowering agent, including, but not limited to, a miotic, an alpha or alpha/beta adrenergic agonist, a beta-blocker, a $Ca^{2+}$ channel blocker, a carbonic anhydrase inhibitor, cholinesterase inhibitor, a prostaglandin agonist, a prostaglandin, a prostamide, a cannabinoid, and combinations thereof.

In some embodiments, a method of treating or ameliorating an ophthalmic disease, such as, but not limited to, glaucoma in a subject, includes treatment with V-VIS (e.g., utilizing one or more of the exemplary V-VIS devices and methods) in combination with administering a therapeutically effective amount of a pharmacological agent decreasing retinal ganglion cell dysfunction and/or pathology, related to ischemia or excitotoxicity.

In some embodiments, a method of treating or ameliorating an ophthalmic disease, including, but not limited to, glaucoma in a subject, includes treatment with V-VIS (e.g., utilizing one or more of the exemplary V-VIS devices and methods) in combination with administering a therapeutically effective amount of a pharmacological agent decreasing excessive excitatory amino acid (EAA) stimulation, including, but not limited to, a glutamate antagonist and/or any combination of a glutamate antagonist and at least one IOL-lowering agent.

In some embodiments, a method of treating or ameliorating an ophthalmic disease, such as, but not limited to, glaucoma in a subject, includes treatment with V-VIS (e.g., utilizing one or more of the exemplary V-VIS devices and methods) in combination with administering a therapeutically effective amount of a pharmacological agent providing neuroprotection and/or neuroregeneration of retinal ganglion cells, including but not limited to a rho-kinase (ROCK) inhibitor or an adenosine receptor agonist.

What is claimed is:

1. A method, comprising:
    delivering to a retina of an eye, using a device comprising one or more layers and located anterior to the retina, environmental light from an ocular field of view, the delivering comprising delivering approximately collimated environmental light through one or more collimating apertures in the one or more layers, and the one or more collimating apertures generating a moving aperture effect at a rate of at least 50 hertz based on a speed of fixational movements of the eye.

2. The method of claim 1, wherein the one or more collimating apertures are surrounded by at least one area varying from the one or more collimating apertures in at least one of defocus, index of refraction or optics.

3. A method, comprising:
    delivering, to a retina of an eye, and using a device comprising one or more layers and located anterior to the retina, environmental light from an ocular field of view, and adjusting the one or more layers of the device, the one or more adjusted layers comprising one or more collimating apertures, the one or more collimating apertures being surrounded by at least one area varying from the one or more collimating apertures in at least one of defocus, index of refraction or optics, and the one or more collimating apertures generating a moving aperture effect at a rate of at least 50 hertz based on a speed of fixational movements of the eye.

* * * * *